(12) United States Patent
Goto et al.

(10) Patent No.: US 7,063,659 B2
(45) Date of Patent: Jun. 20, 2006

(54) ENDOSCOPE TREATMENT-TOOL, ENDOSCOPE DEVICE, TREATMENT-TOOL FIXING METHOD AND CATHETER-REPLACING METHOD

(75) Inventors: Hiroaki Goto, Hachioji (JP); Tsuyoshi Nakagawa, Hachioji (JP); Kenji Shibaki, Hachioji (JP); Junichi Muramatsu, Akiruno (JP); Seiko Yunoki, Fussa (JP)

(73) Assignee: Olympus Corporation, Tokyo (JP)

( * ) Notice: Subject to any disclaimer, the term of this patent is extended or adjusted under 35 U.S.C. 154(b) by 200 days.

(21) Appl. No.: 10/456,413

(22) Filed: Jun. 6, 2003

(65) Prior Publication Data
US 2004/0049095 A1    Mar. 11, 2004

(30) Foreign Application Priority Data
Jun. 7, 2002  (JP) .............................. 2002-166900
Jun. 3, 2003  (JP) .............................. 2003-157733

(51) Int. Cl.
*A61B 1/00*  (2006.01)
(52) U.S. Cl. .................... 600/104; 600/106; 600/107
(58) Field of Classification Search ........ 600/104–107, 600/117, 153, 154
See application file for complete search history.

(56) References Cited

U.S. PATENT DOCUMENTS

| | | | |
|---|---|---|---|
| 4,706,655 A | * | 11/1987 | Krauter ...................... 600/106 |
| 5,084,022 A | | 1/1992 | Claude |
| 5,379,779 A | | 1/1995 | Rowland et al. |
| 6,827,718 B1 | * | 12/2004 | Hutchins et al. .............. 606/47 |

FOREIGN PATENT DOCUMENTS

| | | |
|---|---|---|
| JP | 2002-34905 | 2/2002 |
| JP | 2003-93516 | 4/2003 |

* cited by examiner

*Primary Examiner*—Beverly M. Flanagan
(74) *Attorney, Agent, or Firm*—Scully, Scott, Murphy & Presser, P.C.

(57) ABSTRACT

An endo-therapy accessory is used in combination with an endoscope which has a forceps elevator. This endo-therapy accessory has an insertion portion of the endo-therapy accessory to be inserted into the endoscope. The insertion portion of the endo-therapy accessory has a forceps elevator fixing section set in a range of passing the elevator, and fixed when the elevator is lifted, and a main index for use in determining whether a part of the elevator fixing section, which is more proximal than a far end of the fixing portion, is located on the elevator.

12 Claims, 16 Drawing Sheets

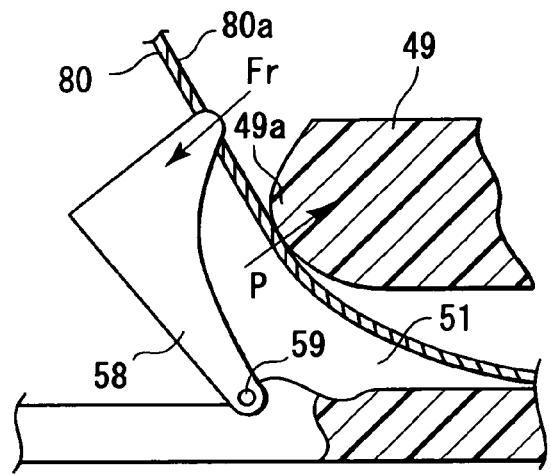
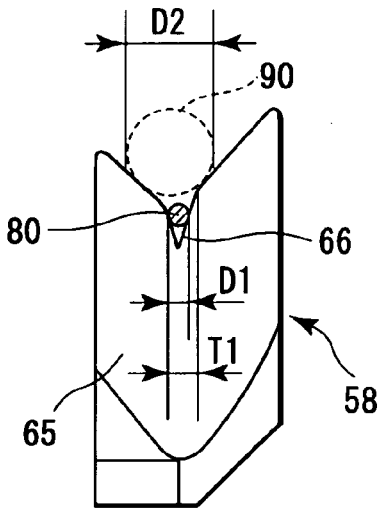
FIG. 4A  FIG. 4B
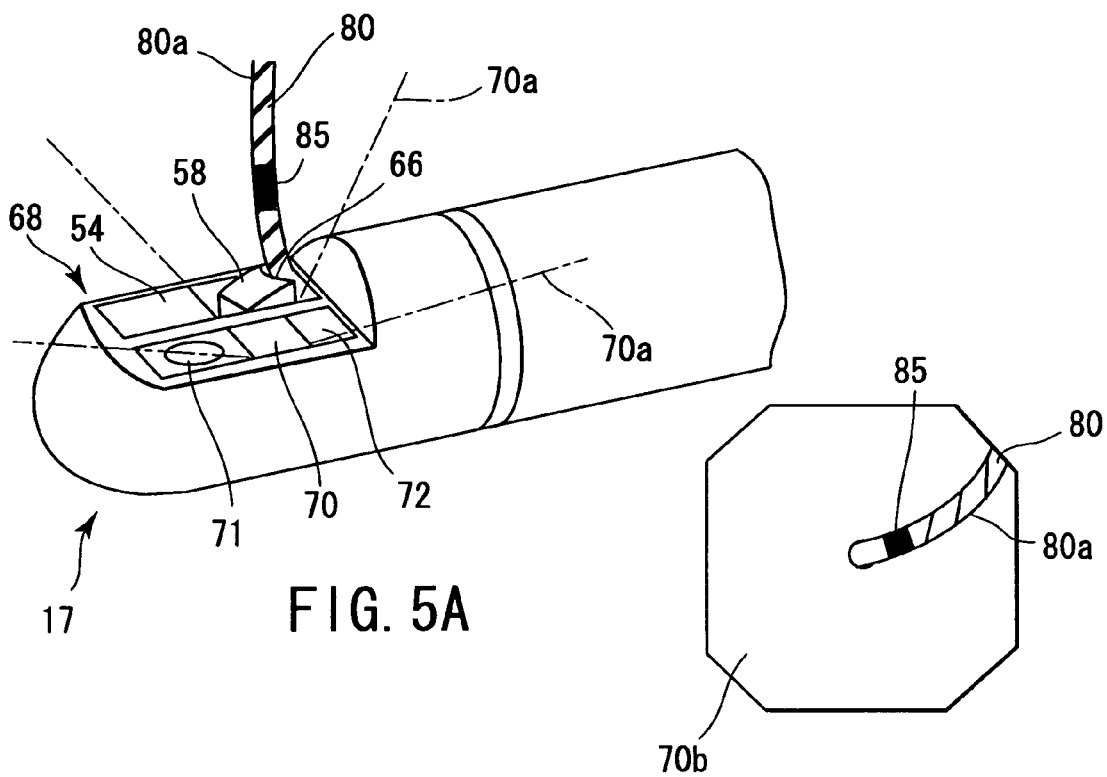
FIG. 5A  FIG. 5B

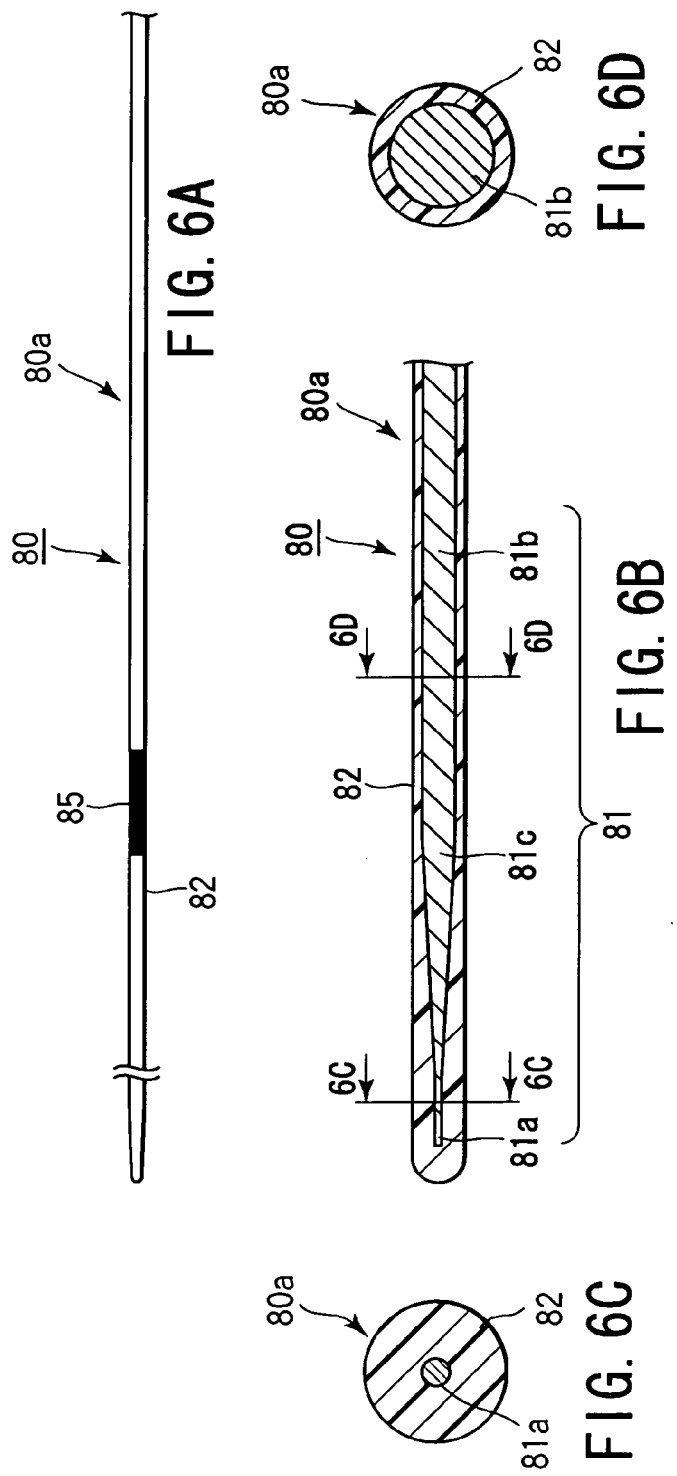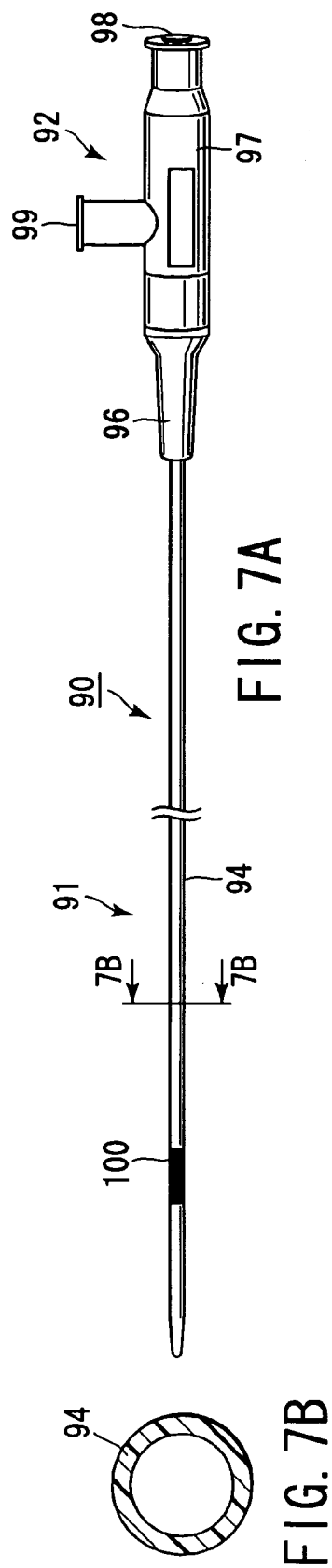

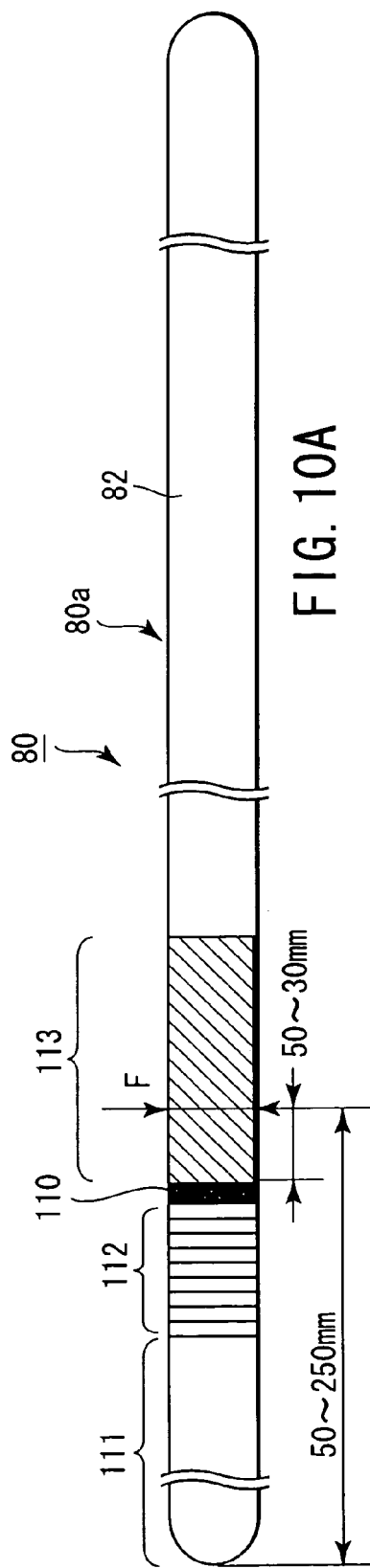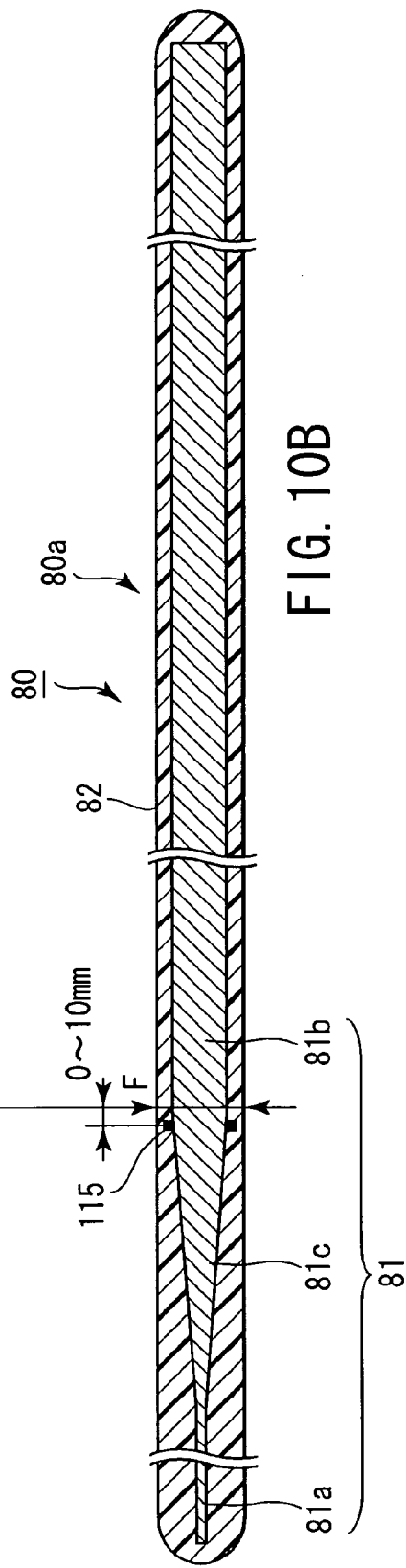

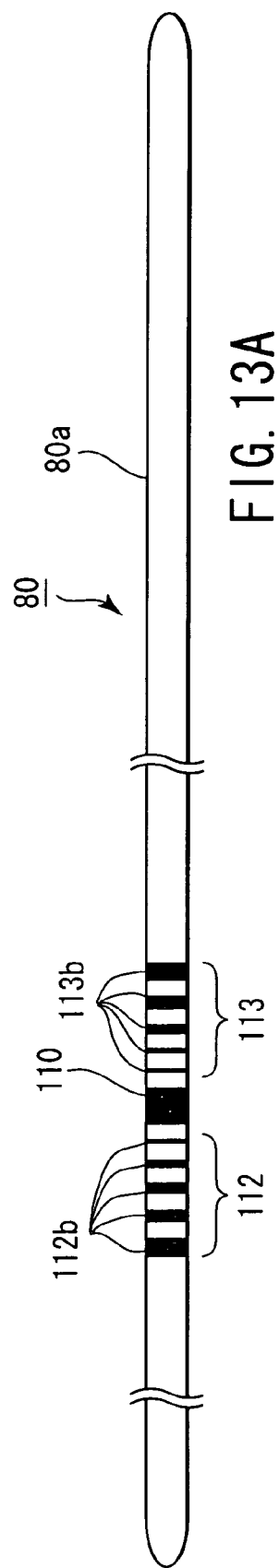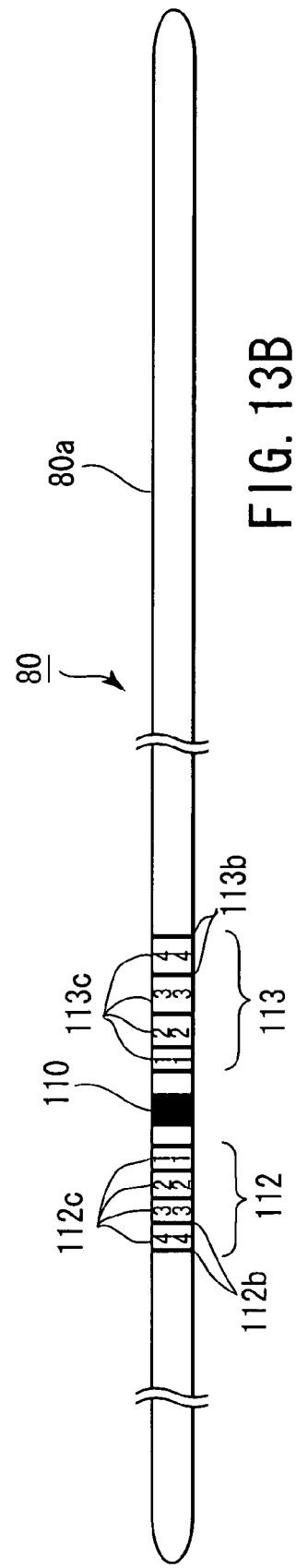

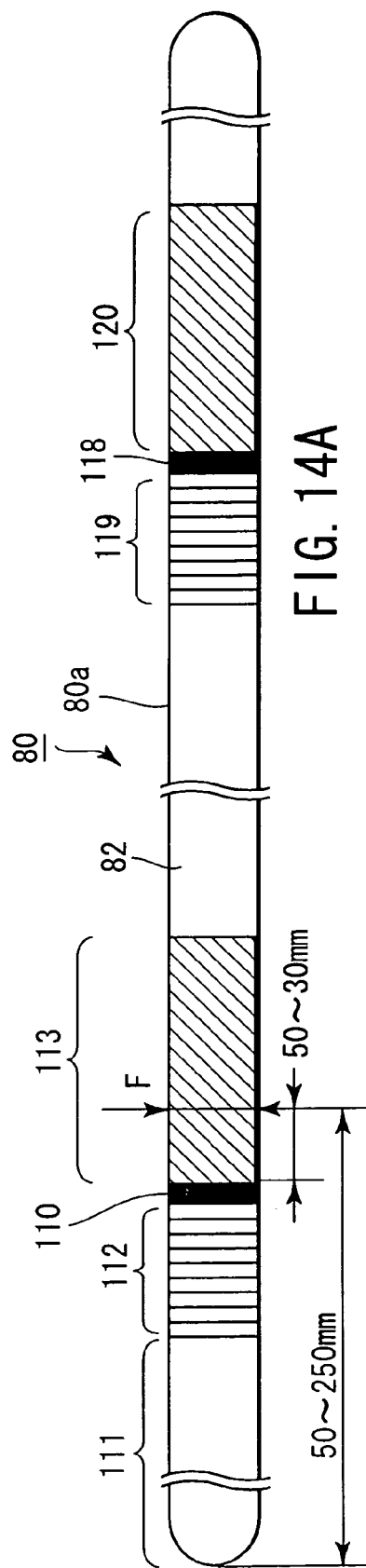
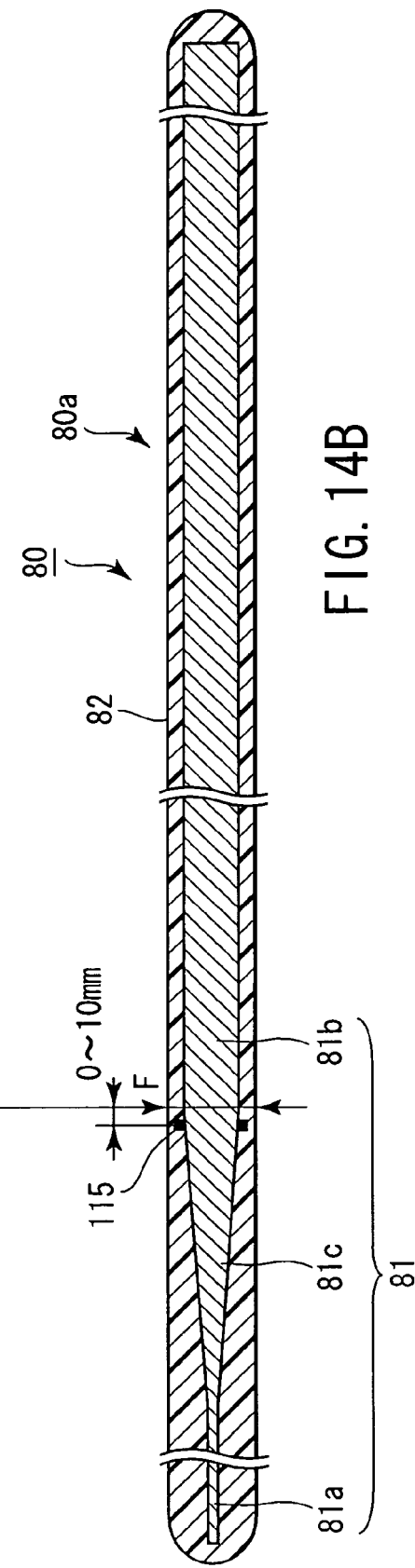
FIG. 14A
FIG. 14B

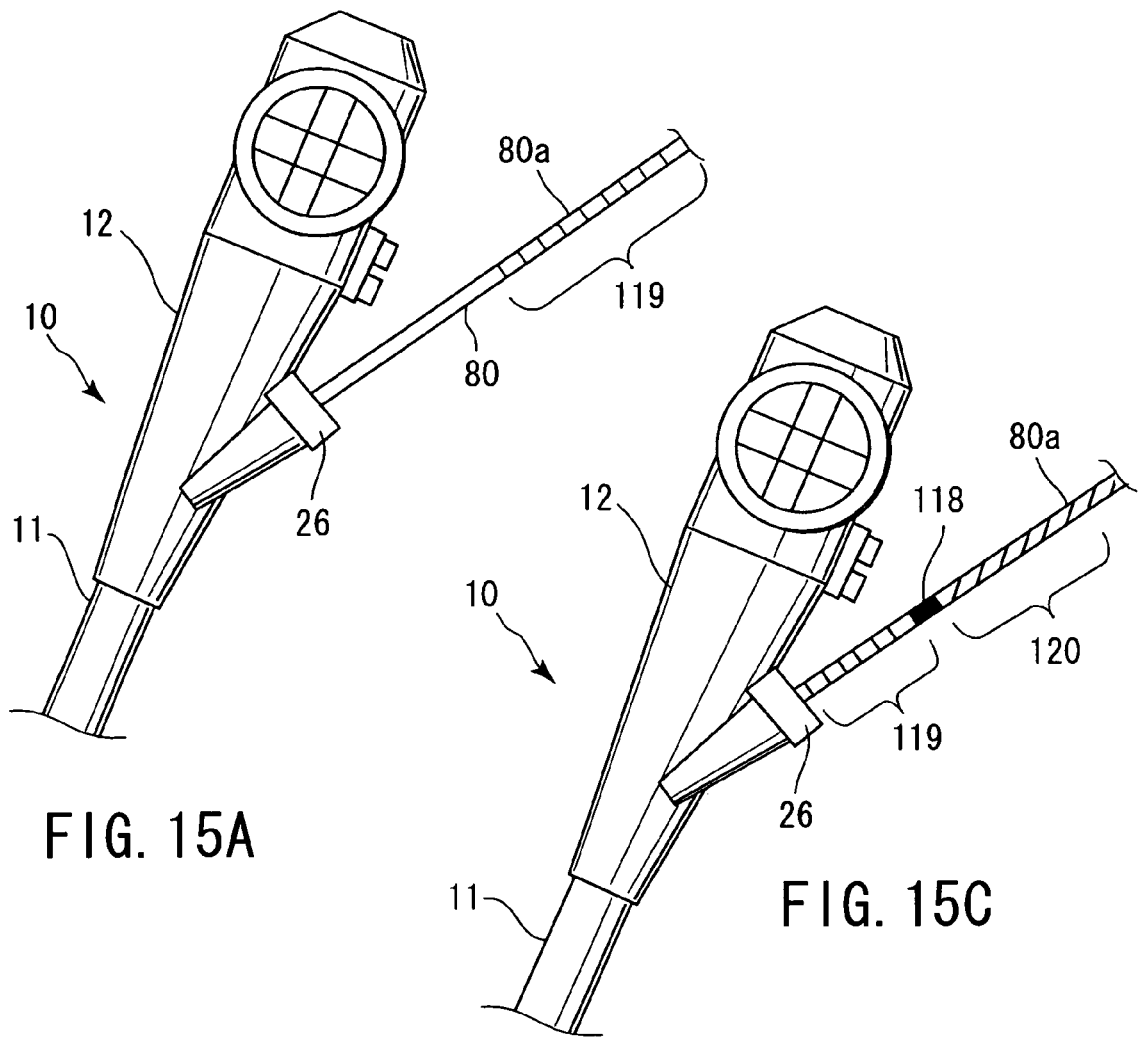
FIG. 15A
FIG. 15C
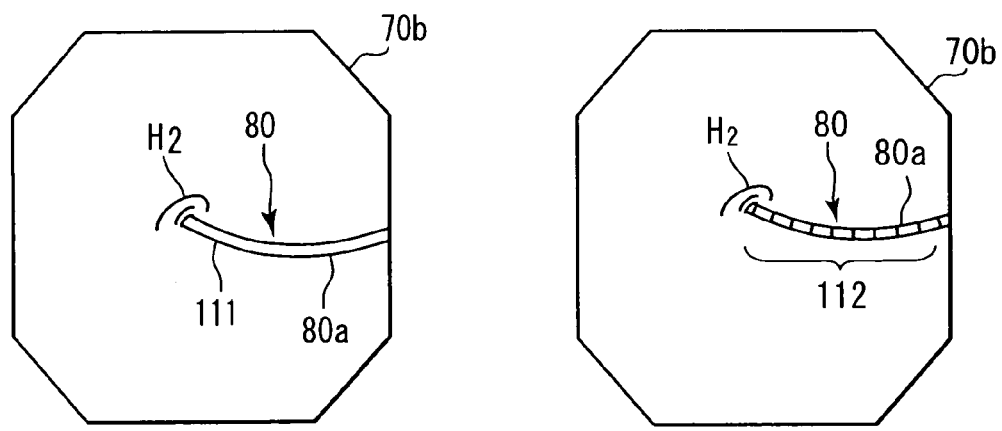
FIG. 15B
FIG. 15D

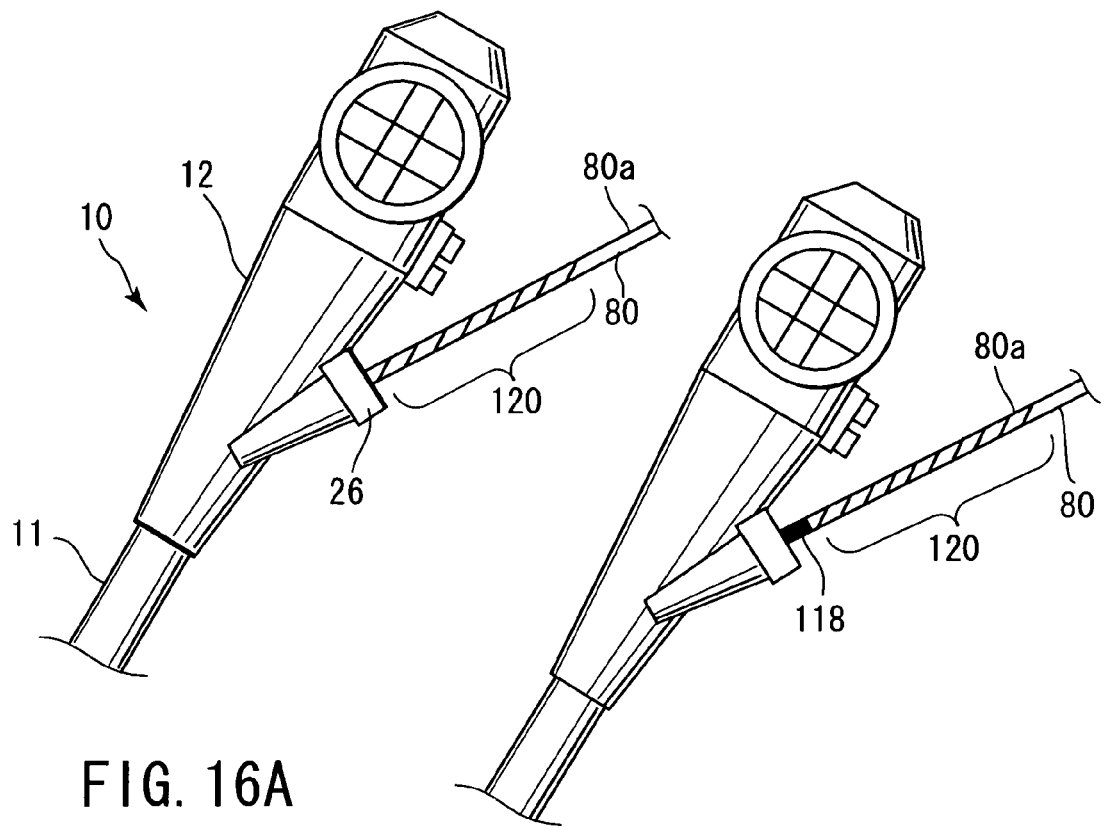
FIG. 16A
FIG. 16C
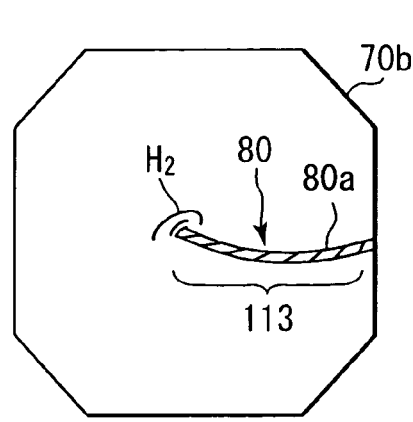
FIG. 16B
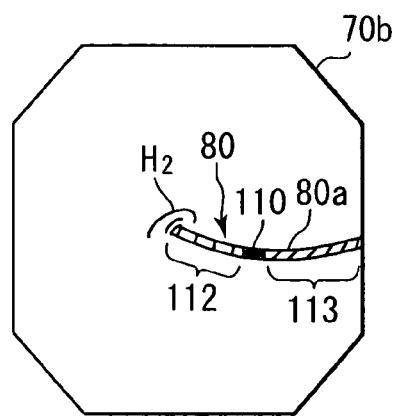
FIG. 16D

ENDOSCOPE TREATMENT-TOOL, ENDOSCOPE DEVICE, TREATMENT-TOOL FIXING METHOD AND CATHETER-REPLACING METHOD

CROSS-REFERENCE TO RELATED APPLICATIONS

This application is based upon and claims the benefit of priority from the prior Japanese Patent Applications No. 2002-166900, filed Jun. 7, 2002; and No. 2003-157733, filed Jun. 3, 2003, the entire contents of which are incorporated herein by reference.

BACKGROUND OF THE INVENTION

1. Field of the Invention

The present invention relates to an endo-therapy accessory which is used through an endoscope, an endoscopic device where an endoscope and an endo-therapy accessory are combined to be used, endo-therapy accessory fixing method, and catheter exchange method.

2. Description of the Related Art

A disease in a patient's pancreatic/bile duct system or the like is generally treated by an endoscopic treatment which uses an endoscope. For the treatment of the pancreatic/bile duct system which uses the endoscope, in addition to a diagnostic treatment for imaging a bile duct or a pancreatic duct endoscopically, for example, there is a curative treatment for collecting calculus present in a choledoch duct by using a balloon or forceps, etc.

To carry out such a treatment, a guide wire is used as an endo-therapy accessory to approach the pancreatic/bile duct from a duodenal papilla. The guide wire which is generally used is formed such that a tip side part is processed to be tapered or thin in diameter, and flexibility of the tip side part is increased.

The guide wire is used when the endo-therapy accessory is guided (passed) into a portion of a narrow duct mainly such as a papilla or a stricture, or when the endo-therapy accessory is changed. In the case of carrying out an endoscopic treatment for the pancreatic duct, the bile duct or the like by using the guide wire, specifically the following work must be carried out.

This treatment necessitates at least two operators, i.e., a main operator 201 and an assistant operator 202 as shown in FIG. 20A and FIG. 20B. The main operator 201 operates the endo-therapy accessory out of a biopsy valve 219 of an endoscope 210 by a right hand while gripping an operation section 212 of the endoscope 210. The assistant operator 202 has a role to assist the main operator 201.

As shown in FIGS. 20A and 20B, the main operator 201 inserts a tip 214 of an insertion portion 213 of the endoscope 210 near a duodenal papilla beforehand. After checking of insertion of a tip 214 near a papilla of a duodenum, the main operator 201 inserts a catheter 216 through an endo-therapy accessory channel disposed in the insertion portion 213 of the endoscope 210 from the biopsy valve 219 of the endoscope 210 to project a tip part 216b of the catheter 216 from a tip 214 of the insertion portion 213 of the endoscope 210, and passes the tip part 216b of the catheter 216 from the papilla through a stricture or a stone in a pancreatic duct or a bile duct to a desired position. The main operator 201 or the assistant operator 202 inserts a guide wire 218 from a valve 216a of a rear side of the catheter 216 inserted through the endoscope into a pancreatic duct or a bile duct through an inner hole of the catheter 216 toward a tip of the catheter 216.

After a tip of the guide wire 218 is projected from a tip 216b of the catheter 216, the tip of the guide wire 218 is inserted through the papilla into the pancreatic duct or the bile duct. Then main operator 201 checks the sufficient insertion of the tip of the guide wire 218 to the desired position in the pancreatic duct or the bile duct under X-rays. Alternatively, for example, if the catheter 216 cannot pass through a very narrow duct part such as the stricture or the stone in the pancreatic duct or the bile duct because the tip of the guide wire 218 is small in diameter or flexible, the guide wire 218 is preferentially inserted into a desired position, and then the catheter 216 is guided by using the guide wire as a guiding tool.

When another treatment is carried out after the end of the treatment which uses the catheter 216, the endo-therapy accessory is changed. The main operator 201 pulls the catheter 216 from the endo-therapy accessory channel of the endoscope 210 in a state where the guide wire is detained from the papilla into the pancreatic duct or the bile duct. When the main operator 201 pulls out the catheter 216 from the endo-therapy accessory channel of the insertion portion 213 of the endoscope 210, a friction force is generated between the catheter 216 and the guide wire 218 to pull the guide wire 218 integrally to the hand side. At this time, delicate collaborative work is carried out: the main operator 201 pulls the catheter 216 to the hand side by 20 mm while the assistant operator 202 inserts the guide wire 218 into the catheter 216 relatively by 20 mm (actually not moved). To carry out this work, the main operator 201 and the assistant operator 202 must carefully work in close cooperation.

During this work, as shown in FIG. 20B, when the tip 216b of the catheter 216 comes out of the biopsy valve 219 of the operation section 212 side of the endoscope 210, the main operator 201 grips the rear end side of a guide wire 218 near the biopsy valve 219 of the endoscope 210 so as to prevent falling-off of the tip of the guide wire 218 from the inserted position. The assistant operator 202 pulls out the catheter 216 from the rear end of the guide wire 218. By such work, the catheter 216 is pulled out from the endo-therapy accessory channel while the guide wire 218 is left in the desired position.

Then, the rear end side of the guide wire 218 is inserted into an insertion hole of another endo-therapy accessory in place of the catheter 216 and, by using the guide wire 218 as a guiding tool, this endo-therapy accessory is inserted into the endo-therapy accessory channel of the insertion portion 213 of the endoscope 210. The endo-therapy accessory is guided into the pancreatic duct or the bile duct by the guide wire 218. Thereafter, work of inserting/pulling-out the endo-therapy accessory in a state where the guide wire 218 is left in a desired position is repeated by the number of times of exchanging the endo-therapy accessory.

Incidentally, for example, U.S. Pat. No. 5,084,022, U.S. Pat. No. 5,379,779, and Jpn. Pat. Appln. KOKAI Publication No. 2003-93516, there is disclosed a technology which has markings (indexes) formed on a guide wire to measure an insertion length disposed in an insertion portion of an endoscope, a lead-out length from a tip of the endo-therapy accessory channel etc.

The specification of U.S. Pat. No. 5,084,022 discloses a technology which has markings formed at equal intervals along a longitudinal direction of a guide wire. Each marking is disposed in a streaky shape in a circumferential direction of the guide wire. For the markings, the number of streaks is gradually increased toward a hand side of the guide wire. As a distance from a tip of the guide wire to a position of the marking is known beforehand, the number of marking streaks observed from a distal end of the endoscopic insertion portion is checked by an observation monitor to measure a distance from the tip of the guide wire. That is, when such a guide wire is used, a marking projected from a papilla to a proximate side is checked by a monitor of the endoscope in a state where the tip of the guide wire is arranged in a treatment/diagnosis position of the pancreatic/bile duct. By using this monitor to check on the number of marking streaks, a distance from the treatment/diagnosis position to the papilla is measured.

The specification of U.S. Pat. No. 5,379,779 discloses a technology of a guide wire which has radiopaque markings. This guide wire is used to measure a length of the inside of the papilla which cannot be checked by the endoscopic monitor. By checking on the tip of the guide wire, the papilla and radiopaque markings on the guide wire of the papilla portion, a projected length of the guide wire from the tip of the endo-therapy accessory or the like is measured.

In Jpn. Pat. Appln. KOKAI Publication No. 2003-93516, markings are disposed in positions where structural characteristics of the guide wire are changed. Thus, when the guide wire is observed through the endoscope, the positions of structural characteristic changes of the guide wire are easily recognized visually.

Additionally, Jpn. Pat. Appln. KOKAI Publication No. 2002-34905 discloses an endoscope which can lock a guide wire having flexibility. An endo-therapy accessory elevator is disposed in a distal end of an insertion portion of the endoscope of this technology. A V-shaped wire-locking groove is disposed in the endo-therapy accessory elevator. If the forceps elevator is lifted while the guide wire is arranged in the wire-locking groove, the guide wire is bent, and locked by a reactive force generated when the bent guide wire returns to its original state. Accordingly, certain hardness is necessary to lock the guide wire. When work is carried out by using this endoscope to pull out the catheter from the endo-therapy accessory channel, in a state where a tip of the catheter is pulled into a distal end of the endoscope, the forceps elevator is lifted to lock only the guide wire thereon. Since the guide wire is locked on the forceps elevator not to be moved, in work thereafter, the main operator can leave the guide wire in a desired position by pulling out the catheter. That is, it is not necessary for the assistant operator to carry out work of relatively inserting the guide wire into the guide catheter.

BRIEF SUMMARY OF THE INVENTION

According to an aspect of the present invention, an endo-therapy accessory is used in combination with an endoscope which has a forceps elevator. This endo-therapy accessory includes the following: an insertion section of the endo-therapy accessory to be inserted into the endoscope; the insertion section of the endo-therapy accessory includes a forceps elevator fixing section in a range of passing the elevator and fixed when the elevator is raised, and a main index for use in determining whether a part of the elevator fixing section, which is more proximal than a far end of the fixing portion, is located on the elevator.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4A is a schematic vertical sectional view showing a locked state of a guide wire in the distal end of the insertion portion of the endoscope.

FIG. 4B is a front view of an endo-therapy accessory elevator.

FIG. 5A is a schematic perspective view showing the distal end of the insertion portion of the endoscope.

FIG. 5B is a view of a monitor screen for displaying a locked state of the guide wire on the endo-therapy accessory elevator shown in FIG. 5A.

FIG. 6A is an appearance view of the guide wire in the endoscopic device of the first embodiment.

FIG. 6B is a vertical sectional view of the guide wire in the endoscopic device of the first embodiment.

FIG. 6C is a sectional view cut along the 6C—6C line of the guide wire shown in FIG. 6B.

FIG. 6D is a sectional view cut along the 6D—6D line of the guide wire shown in FIG. 6B.

FIG. 7A is an appearance view of a catheter in the endoscopic device of the first embodiment.

FIG. 7B is a sectional view cut along the 7B—7B line of the catheter shown in FIG. 7A.

FIG. 10A is a side view of a guide wire in the endoscopic device of the second embodiment.

FIG. 10B is a vertical sectional view of the guide wire shown in FIG. 10A.

FIG. 13A is a schematic view showing a state where the third and fourth marking portions of a guide wire are deformed in the endoscopic device of the second embodiment.

FIG. 13B is a schematic view showing a state where the third and fourth marking portions of the guide wire are deformed in the endoscope of the second embodiment.

FIG. 14A is a side view of a guide wire in an endoscopic device according to a third embodiment.

FIG. 14B is a vertical sectional view of the guide wire shown in FIG. 14A.

FIG. 15A is a schematic view showing a hand side in an endoscope of the endoscopic device of the third embodiment where a sixth marking portion is arranged from a biopsy valve to a rear side.

FIG. 15B is a schematic view showing an image on endoscopic observation monitor displayed when a guide wire is in a state shown in FIG. 15A.

FIG. 15C is a schematic view showing the hand side in the endoscope of the endoscopic device of the third embodiment where the sixth marking portion coincides with a base end of the biopsy valve.

FIG. 15D is a schematic view showing an image on the endoscopic observation monitor displayed when the guide wire is in a state shown in FIG. 15C.

FIG. 16A is a schematic view showing the hand side in the endoscope of the endoscopic device of the third embodiment where a seventh marking portion coincides with the base end of the biopsy valve.

FIG. 16B is a schematic view showing an image on the endoscopic observation monitor, displayed when the guide wire is in a state shown in FIG. 16A.

FIG. 16C is a schematic view showing the hand side in the endoscope of the endoscopic device of the third embodiment where a fifth marking portion coincides with the base end of the biopsy valve.

FIG. 16D is a schematic view showing the endoscopic observation monitor displayed when the guide wire is in a state shown in FIG. 16C.

DETAILED DESCRIPTION OF THE INVENTION

The embodiments of the present invention will be described with reference to the accompanying drawings.

Figure 1:
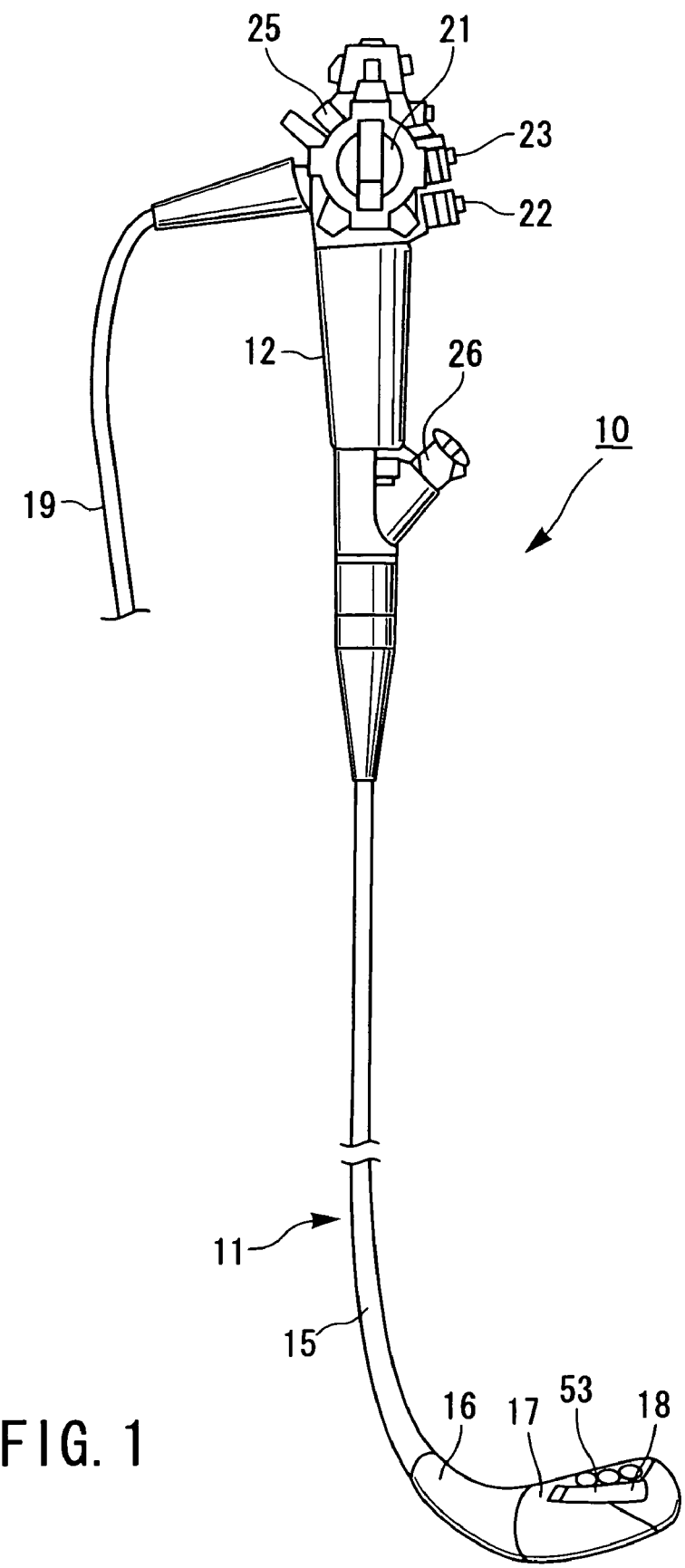
FIG. 1 is a schematic appearance view showing an endoscope in an endoscopic device (endo-therapy accessory) according to a first embodiment.

First, a first embodiment will be described by referring to FIGS. 1 to 8. As shown in FIG. 1, an endoscope 10 of the embodiment includes a thin and long insertion portion 11 inserted into a body cavity, and an operation section 12 connected to a rear end of the insertion portion 11. The insertion portion 11 includes a thin and long tube portion 15 having flexibility, a bending portion 16 connected to a tip of the flexible tube portion 15, and a hard distal end 17 arranged in an utmost tip position of the insertion portion 11. The insertion portion 11 includes an endo-therapy accessory channel 52 through which an endo-therapy accessory is inserted, an illumination optical system for illuminating an object to be treated, and an observation optical system for observing the illuminated object to be treated. The observation optical system includes an objective lens 70 in a distal end 17 of the insertion portion 11, and the illumination optical system includes an illumination lens 71 in the distal end 17 of the insertion portion 11. In the observation optical system, for example, a not-shown CCD element is disposed to pick up an image of a light made incident on the objective lens 70. The CCD element is electrically connected to the operation section 12. In the insertion portion 11, preferably, an air/water channel is further disposed side by side with the endo-therapy accessory channel 52. The endoscope 10 of the embodiment is formed as a so-called side view type where an observation visual field direction of the objective lens in the tip 70 is in an inclined direction, for example, orthogonal to an axial direction of the insertion portion 11.

On the other hand, a rear end of a universal cord 19 is connected to the operation section 12 of the endoscope 10. In a tip of the universal cord 19, a light guide tube is disposed to guide a light to the illumination optical system, and an electric contact section (not shown) is disposed to be electrically connected through the operation section 12 to the CCD element of the observation optical system. The light guide tube and the electric contact section are respectively connected to a light source device and an image-processing device (not shown) which are external devices. That is, the light source device emits an illumination light, which is passed through the light guide tube and the illumination optical system to irradiate the object to be treated from the illumination lens 71. The object irradiated with the light is illuminated, and an image of the illumination light is picked up by the CCD element through the objective lens 70.

The image picked up by the CCD element is transmitted from the observation optical system through the electric contact section to the image-processing device. An endoscopic observation monitor 70b (see FIG. 5B) is connected to the image-processing device, and the endoscopic observation image picked up by the CCD element is displayed on the monitor 70b.

In the operation section 12 of the endoscope 10, a bending operation section 21 for bending a bending portion 16 of the insertion portion 11 up-and-down and left-and-right by a remote control operation, an air/water supply button 22, and a suction operation button 23 are disposed. The air/water supply button 22 is used when the objective lens 70 and the illumination lens 71 disposed in the distal end 17 of the air/water channel are washed to remove stains stuck to the lenses 70, 71, thereby facilitating visual recognition of an organ of a body to be treated (organism). The suction operation button 23 is used when blood or tissues accumulated during the treatment are discharged through the suction channel to the outside of the body.

The bending operation section 21 is arranged in the operation section 12 in a state where it is projected in a direction roughly orthogonal to a center axial direction of the insertion portion 11. In a position adjacent to this bending operation section 21, a elevator operation knob 25 is disposed to lift a later-described forceps elevator 58 (see FIG. 3A). In the vicinity of the connection portion between the insertion portion 11 and the operation section 12, a biopsy valve (insertion port) 26 is arranged to be communicated with the endo-therapy accessory channel 52.

Figure 2A:
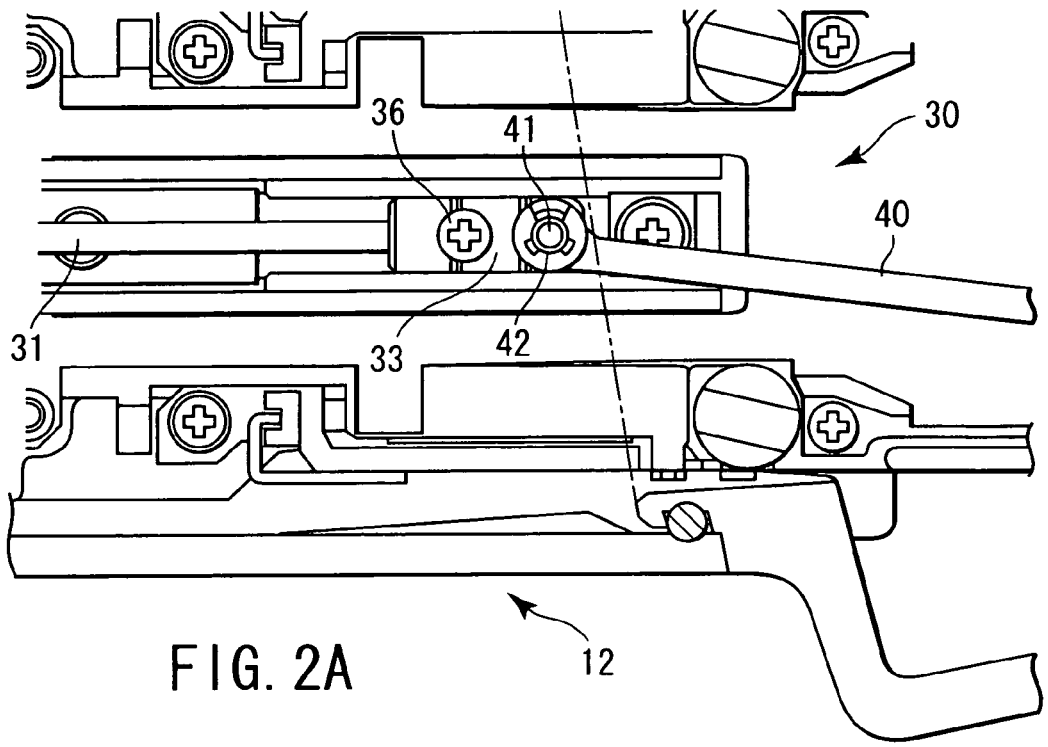
FIG. 2A is a plan view of main sections showing an elevator operation mechanism incorporated in an operation section of the endoscope.
Figure 2B:
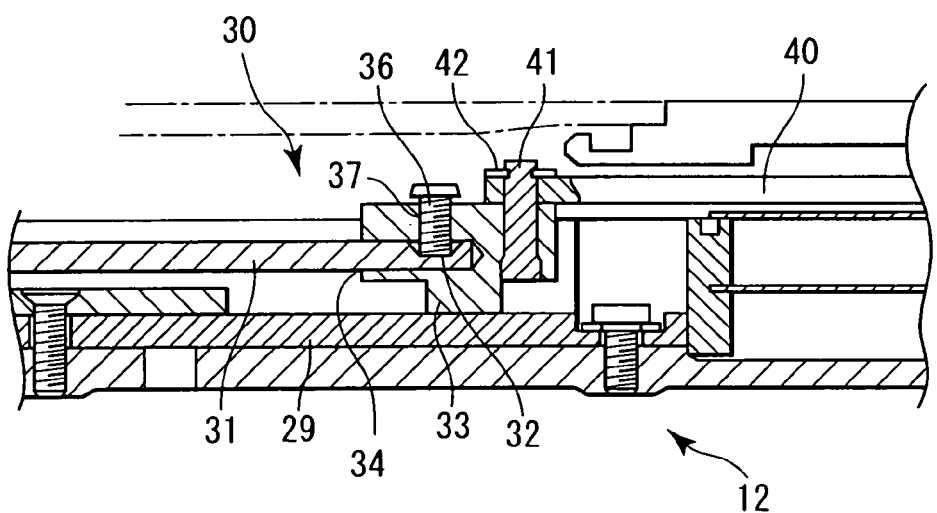
FIG. 2B is a vertical sectional view of main sections showing the elevator operation mechanism incorporated in the operation section of the endoscope.

As shown in FIG. 2B, inside the operation section 12, a base 29 is arranged to become a foundation for the operation section 12. An elevator operation mechanism 30 is fixed on the base 29 to operate a later-described wire 61 (see FIG. 3A) connected to the forceps elevator 58. That is, inside the operation section 12, the elevator operation mechanism 30 is incorporated to operate the lift wire 61. A wire-fixing member 31 made of a hard bar-shaped material such as a metallic material shown in FIGS. 2A and 2B is integrally fixed to a rear end of the lift wire 61 by, e.g., solder. As shown in FIG. 2B, a locking groove 32 is formed in a recessed shape in a rear end of the wire-fixing member 31.

As shown in FIGS. 2A and 2B, a link member 33 made of a hard block body such as a metallic material is fixed to the rear end of the wire-fixing member 31. An insertion hole 34 of the wire-fixing member 31 is formed in the link member 33. The rear end of the wire-fixing member 31 is fitted into the insertion hole 34. Here, an entire range of the rear end of the wire-fixing member 31 where the locking groove 32 is formed is fitted into the insertion hole 34 of the link member 33.

In the link member 33, a female screw 37 is disposed to be engaged with a fixing screw 36 of the wire-fixing member 31. A tip of the fixing screw 36 engaged with the female screw 37 of the link member 33 is inserted into the locking groove 32 of the wire-fixing member 31. Thus, the wire-fixing member 31 is connected in a state of being fixed to the link member 33.

Such a link member 33 is arranged so as to freely move back and forth in a longitudinal direction of the base 29. One end of an arm 40 is rotatably connected to the link member 33 by a link shaft 41 which is a bar-shaped shaft member. A snap ring (locking member) formed in a C shape or an E shape is engaged with an end of the link shaft 41 far from the base 29.

The other end of the arm 40 is connected to the elevator operation knob 25 disposed adjacently to the bending operation section 21. Accordingly, the elevator operation knob 25 in the operation section 12 is operated to pull the lift wire 61 sequentially through the arm 40, the link member 33 and the wire-fixing member 31.

Figure 3A:
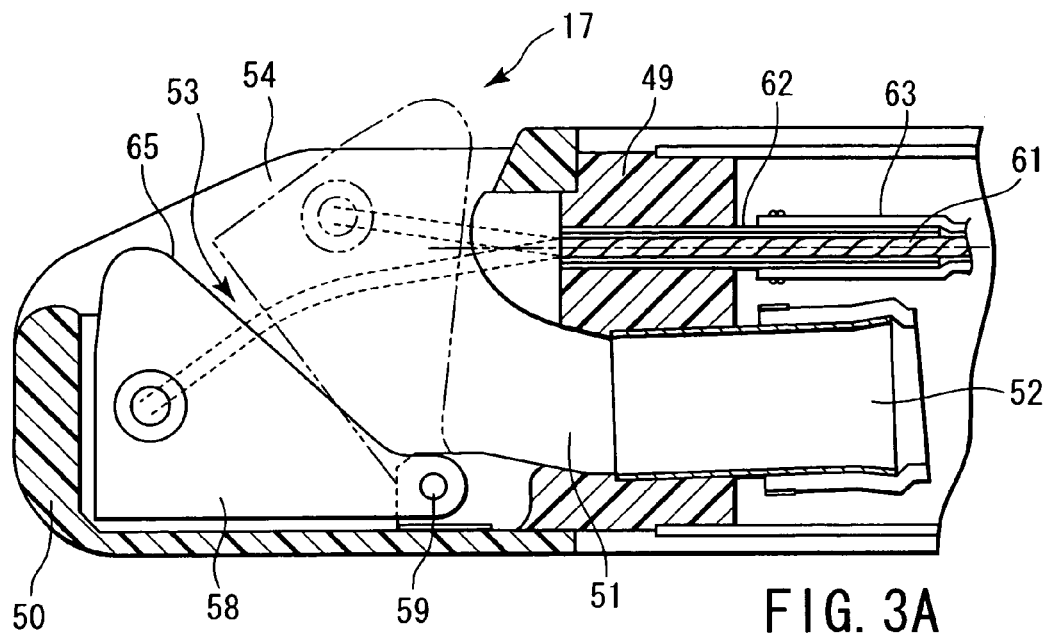
FIG. 3A is a schematic vertical sectional view showing a constitution of a tip of an insertion portion of the endoscope.
Figure 3B:
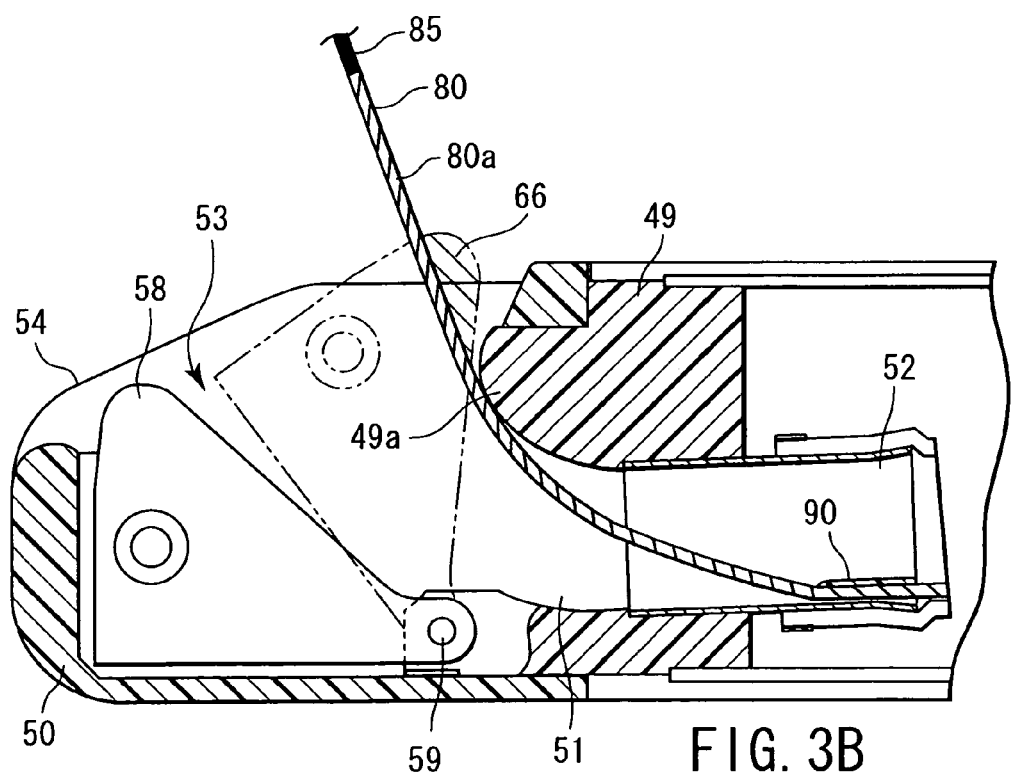
FIG. 3B is a schematic vertical sectional view showing a constitution of the distal end of the insertion portion of the endoscope in a position different from that of FIG. 3A.

As shown in FIGS. 3A and 3B, in the distal end 17 of the endoscope 10, a tip hard portion 49 and a tip cover 50 made of a nonconductive material (insulating material) such as a resin material to cover the surrounding of the tip hard portion 49 are disposed. The tip cover 50 is fixed to the tip hard portion 49 by an adhesive or the like. In the tip hard portion 49, a guide path (introduction guide path) 51 is formed to guide (introduce) an endo-therapy accessory such as a later-described guide wire 80 to the tip side. This guide path 51 is formed to be continuous from the endo-therapy accessory channel (insertion hole) 52 as an endo-therapy accessory insertion guide path arranged in the insertion portion 11 of the endoscope 10. In a tip side of the guide path 51, a housing chamber 53 is disposed which is a space formed by the tip hard portion 49 and the tip cover 50. A channel opening 54 is formed in this housing chamber 53 to form a tip opening of the endo-therapy accessory channel 52.

In the housing chamber 53, the forceps elevator 58 is arranged as a locking mechanism to lift an endo-therapy accessory such as forceps, a later-described catheter 90 or a guide wire 80 introduced through the channel 52 to lead it from the channel opening 54 to the outside. One end of the forceps elevator 58 is pivotally attached to an elevator rotation supporting point 59 disposed in the tip hard portion 49. This elevator rotation supporting point 59 is arranged in a location below the tip opening of the guide path 51.

As shown in FIG. 3A, a tip of the lift wire 61 is fixed to the forceps elevator 58. The lift wire 61 is guided through a guide pipe 62 and a guide tube 63 inserted into the insertion portion 11 to the operation section 12 side. A rear end of this lift wire 61 is connected to the wire-fixing member 31 of the elevator operation mechanism 30. When the lift wire 61 is pulled, the forceps elevator 58 is rotated around the elevator rotation supporting point 59 to be freely lifted between an endo-therapy accessory standby position indicated by a solid line and an endo-therapy accessory lift position indicated by a virtual line in FIG. 3A in the housing chamber 53. When the lift wire 61 is pulled to the maximum, the forceps elevator 58 and the tip hard portion 49 are abutted on each other.

As shown in FIG. 4B, a guide surface 65 is formed in the forceps elevator 58 to guide the endo-therapy accessory such as the guide wire 80 or the catheter 90 from the channel opening 54 to the outside. This guide surface 65 is formed in a groove shape which section continuous from the guide path 51 shown in FIG. 4A is formed as a roughly V-shaped groove. In the bottom of the guide surface 65, a slit-shaped wire-locking groove 66 is further formed to detachably lock an appropriate small-diameter member, such as the guide wire 80. That is, a groove width of the guide surface 65 is changed on the bottom. As this wire-locking mechanism 66, preferably, a section narrowed in width in a tapered shape toward the bottom is formed as a roughly V-shaped groove. The wire-locking groove 66 includes two opposing wall surfaces, and a width to allow abutment of not an outer periphery of a member having a large outer diameter D2 such as the catheter 90 but an outer periphery of a member having a small outer diameter D1 such as the guide wire 80.

As shown in FIG. 4B, a relation between an opening slit width (groove width) T1 of the wire-locking groove 66 and the wire diameter D1 of the guide wire 80 is that the wire diameter D1 is set equal to/lower than the opening slit width T1. A relation between the opening slit width T1 and the outer diameter D2 of the other endo-therapy accessory such as the catheter 90 is that the outer diameter D2 of the endo-therapy accessory is set larger than the opening slit width T1.

As shown in FIG. 5A, a recessed notch 68 one side face of which is notched is formed in the outer peripheral surface of the distal end 17. The channel opening 54 is arranged in one side of the notch 68. In a position adjacent to the channel opening 54, the objective lens 70 of the observation optical system and the illumination lens 71 of the illumination optical system are arranged side by side. In a position adjacent to the objective lens 70, an air/water supply port 72 is bored to be communicated with the air/water channel. Accordingly, a light from the light source device and the light guide tube is passed through the illumination optical system, and emitted from the illumination lens 71 to illuminate a desired portion of the test object. The illuminated portion of the test object is passed through the objective lens 70, and an image thereof is picked up by the CCD element of the observation optical system, and sent from the CCD element through the electric contact section to the image-processing device. Then, the inside of the observation visual field 70a of the objective lens 70 shown in FIG. 5A is displayed on the observation monitor 70b shown in FIG. 5B.

According to the embodiment, as shown in FIG. 5A, when the forceps elevator 58 of the endoscope 10 is lifted to the maximum, the guide wire 80 can be checked by the objective lens 70 of the endoscope 10 as shown in FIG. 5B.

The guide wire 80, which is an endo-therapy accessory inserted through the endo-therapy accessory channel 52 of the endoscope 10, is constituted in the following manner. As shown in FIGS. 6A to 6D, the guide wire 80 is formed as a guide wire insertion section 80a which is thin and long as a whole from its tip to its rear end. The insertion section 80a of the guide wire 80 includes a thin and long core material 81, and a cover 82 to cover an outer periphery of the core material 81.

As shown in FIGS. 6B to 6D, the core material 81 of the guide wire insertion section 80a has diameters different between a tip side and a center side. As shown in FIG. 6C, the tip side (tip) of the core material 81 is formed as a small diameter portion (small diameter core material) 81a. As shown in FIG. 6D, the center (insertion section center) side of the core material 81 is formed as a large diameter portion (large diameter core material) 81b slightly larger in diameter than the small diameter portion 81a. As shown in FIG. 6B, the small diameter portion 81a and the large diameter portion 81b are integrally formed by a tapered portion 81c positioned there between. That is, the core material 81 having portions different in diameter (shape or form) is constituted of one member, and formed integrally by the small diameter portion 81a, the large diameter portion 81b and the tapered portion 81c. In order to have flexibility, this core material 81 is made of, e.g., a super-elastic alloy material such as a nickel titanium alloy. For the core material 81, the small diameter portion 81a is formed to be higher in flexibility than the large diameter portion 81b. A rear end of the small diameter portion 81a is equal in flexibility to a tip of the tapered portion 81c, and a rear end of the large diameter portion 81b is equal in flexibility to a rear end of the tapered portion 81c. Thus, as the flexibility-changing portion, the tapered portion 81c is gradually lowered in flexibility from the tip toward the rear end. That is, for the core material 81, the small diameter portion 81a is bent more easily than the large diameter portion 81b, and a force thereof to return to a straight state is weaker.

The cover 82 to cover such a core material 81 is made of, e.g., plastic materials such as polyurethane or PTFE formed, and the core material 81 is covered with this cover 82 without any gap there between. Accordingly, when an external force is applied to the guide wire 80 to bend it, the cover 82 is bent integrally with the core material 81 made of the super-elastic alloy material.

Additionally, the cover 82 has, e.g., non-conductivity (insulation). An outer diameter of the cover 82 which covers the outer periphery of the large diameter portion 81b of the core material 81 is, e.g., about 0.7 mm to 1 mm. On the other hand, an outer diameter of the cover 82 which covers the outer periphery of the small diameter portion 81a of the core material 81 is, e.g., about 0.5 mm to 1 mm. When the outer periphery of the cover 82 of the guide wire 80 is observed by the observation monitor 70b, the guide wire 80 is observed to be similar in outer diameter in any positions, and thus it is difficult to discern the position of the guide wire 80.

As shown in FIG. 6A, a marking (a first main-index) 85 is disposed in a part of the cover 82 of the guide wire 80. This marking 85 is disposed in the outer peripheral surface of the cover 82 which covers the outer periphery from the tip side of the tapered portion 81c to the large diameter portion 81b of the core material 81, for example as shown in FIG. 6B. This marking 85 is disposed to fill the entire range of several millimeters of the cover 82 along an axial direction of the insertion section 80a of the guide wire 80, e.g., 10 mm along the axial direction of the guide wire 80. The marking 85 is colored differently from the cover 82 of the guide wire 80 by, e.g., paint or laser marking. A color of the marking 85 of the guide wire 80 is greatly different from that of the cover 82 and, preferably, the marking 85 is colored to be easily recognized visually on the observation monitor 70b. In addition, in the marking 85, a member made of a material different from that of the cover 82 of the guide wire 80 may be arranged so that it can be easily recognized visually on the observation monitor 70b, for example, a heat-shrinkable tubing which is shrunk to be attached when heat of a predetermined level or higher is applied. Thus, when such a marking enters the observation visual field 70a of the objective lens 70 shown in FIG. 5A of the endoscope 10 to be displayed in the visual field of the observation monitor 70b shown in FIG. 5B, the marking 85 is easily recognized (visually recognized). That is, the marking 85 is formed as a visually recognized marker.

Such a guide wire 80 is inserted through the endo-therapy accessory channel 52 of the endoscope 10. When the marking 85 of the guide wire 80 is visually recognized on the observation monitor 70b of the endoscope 10, it is disposed in a most tip position where the guide wire 80 can be surely locked and fixed by the forceps elevator 58 and the guide path upper surface wall 49a of the tip hard portion 49. This position of the marking 85 is set in the outer periphery of the cover 82 from the tip side of the tapered portion 81c of the core material 81 to the outer periphery of the large diameter portion 81b. That is, it is disposed on a portion of low flexibility. Thus, a portion guided on the guiding surface 65 of the forceps elevator 58 when the marking 85 is observed on the observation monitor 70b is limited to the rear end side of the tapered portion 81c or the covered portion of the outer periphery with the large diameter portion 81b. Thus, the rear end side or the large diameter portion 81b of the tapered portion 81c of the core material 81 of the guide wire 80 guided on the guiding surface 65 is in a position where flexibility is low and a force to return to a straight shape is strong compared with the small diameter portion 81a. That is, when the forceps elevator 58 is rotated to the endo-therapy accessory lift position, the guide wire 80 can be securely locked on the marking 85 of the guide wire 80 or a side closer to the hand.

FIG. 7A shows an appearance of the catheter 90. This catheter 90 includes a thin and long insertion section 91, and an operation section 92 disposed in a rear end of the insertion section 91. The insertion section 91 is made of an insulating material, and constituted of, e.g., a thin and long approximately transparent (translucent) tube sheath 94 having flexibility. An outer periphery of a tip of this tube sheath 94 is tapered to be smaller in diameter than the outer periphery of the center. An inner diameter of the tube sheath 94 is slightly larger than an outer diameter of the cover 82 which covers the outer periphery of the large diameter portion 81*b* of the guide wire 80.

The operation section 92 includes a sheath holding section 96 for holding an outer periphery of a rear end of the tube sheath 94, a cock 97 disposed in a rear end of the holding section 96, and an opening end 98 disposed in an end more rearward than the cock 97. Inner cavities of the opening end 98, the cock 97 and the tube sheath 94 are communicated with one another. An injection port 99 is projected in the cock 97. Liquid supply means such as a not-shown syringe or a liquid supply tube is connected to this injection port 99, and a chemical solution such as an contrast medium is supplied from a tip of the tube sheath 94 to a desired portion of the test object (biomedical tissue). A marking (a first index) 100 is also disposed in the tube sheath 94 of the insertion section 91 of the catheter 90.

The marking 100 is colored differently from the other part of the tube sheath 94 by, e.g., paint or laser marking. A color of the marking 100 of the catheter 90 is greatly different from that of the other part and, preferably, the marking 100 is colored to be easily recognized. In the marking 100, a member different from that of the other part of the catheter 90 is preferably arranged, e.g., a heat-shrinkable tubing. Additionally, since the insertion section 91 is constituted of a translucent tube sheath 94, the marking 100 may be buried inside the tube sheath 94. That is, the marking 100 only needs to be visually recognized by the operator on the observation monitor 70*b* of the endoscope 10.

A position of such a marking 100 is set in, e.g., a position of several centimeters from a small diameter tip of the tube sheath 94 toward the center. Then, for example, a position of the catheter 90 locked between the guide surface 65 and the guide path upper surface wall 49*a* of the tip hard portion 49 is recognized.

A length of the catheter 90 (endo-therapy accessory) is generally set to, e.g., 200 cm by considering a length of the insertion portion 11 of the endoscope 10. The guide wire 80 must be always exposed from the rear end of the catheter to a more rear side in order to relatively insert the endo-therapy accessory (guide wire 80) into the catheter 90 when the catheter 90 is pulled out. Therefore, since a length of the guide wire 80 needs to be greater than a combined length of the length of the insertion portion 11 of the endoscope 10 and the length of the endo-therapy accessory such as the catheter 90, at least about 400 cm is necessary.

Figure 8:
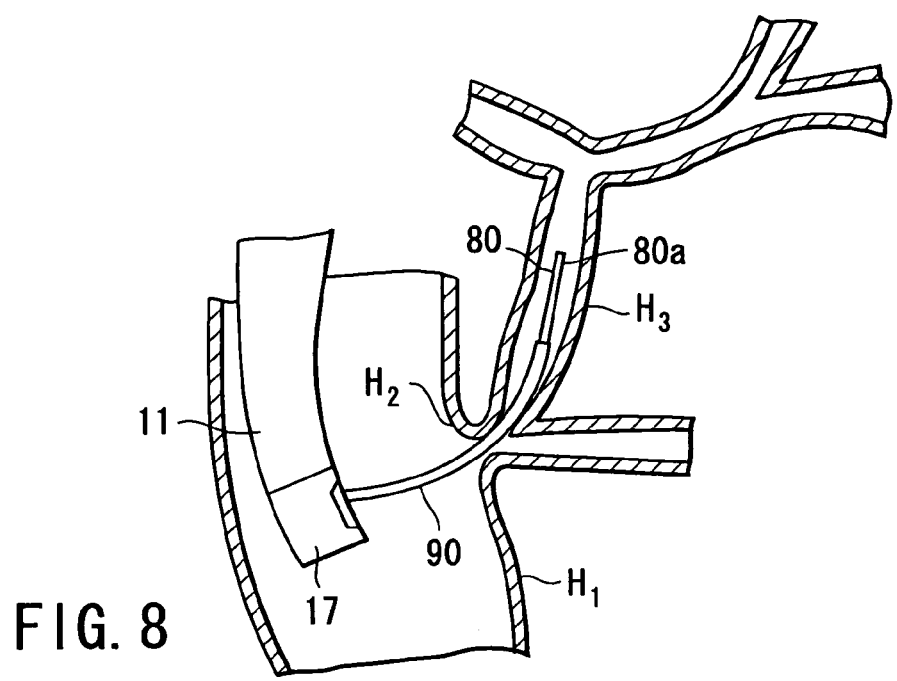
FIG. 8 is a schematic sectional view showing a state of carrying out a treatment by leading out the endoscopic device of the first embodiment from the tip of the insertion portion through the endo-therapy accessory channel.

Next, an operation of the endo-therapy accessory (endoscopic device) of the embodiment will be described by referring to FIG. 8.

As indicated by solid lines in FIGS. 3A and 3B, the forceps elevator 58 disposed in the distal end 17 of the insertion portion 11 is set in an endo-therapy accessory standby position, and the distal end 17 of the insertion portion 11 of the endoscope 10 is inserted near, e.g., a papilla H2 of a duodenum H1 in the body. In this state, as shown in FIG. 3B, the catheter 90 is inserted through the endo-therapy accessory channel 52 into the body. At this time, the catheter 90 is inserted into the papilla H2 of the duodenum H1 in an abutted state on the guiding surface 65 of the forceps elevator 58 while the image picked up by the observation optical system through the objective lens 70 is observed on the observation monitor 70*b*. While the X-ray observation image is observed, the catheter 90 is advanced to pass through a stricture (not shown) in the common bile duct H3, and an contrast medium is injected. The guide wire 80 is passed from the opening end of the rear end of the catheter 90 through the inner hole of the catheter 90, and projected from the tip of the tube sheath 94 of the catheter 90 to be inserted to a desired position in the bile duct.

In a state where the guide wire 80 is retained in the bile duct H3, the catheter 90 is pulled into the guide path 51 of the distal end 17 of the insertion portion 11 of the endoscope 10 or the endo-therapy accessory channel 52 while the observation monitor 70*b* of the endoscope 10 is observed. As shown in FIG. 5A, when the marking 85 of the guide wire 80 is inserted into the observation visual field 70*a* of the objective lens 70, it is displayed on the observation monitor 70*b*. In this state, the elevator operation knob 25 shown in FIG. 1 is operated. This operation is accompanied by pulling of the lift wire 61 shown in FIG. 3A, and the forceps elevator 58 is rotated around the elevator rotation supporting point 59 to be lifted as indicated by a dotted line shown in each of FIGS. 3A and 3B. By this operation, the forceps elevator 58 is lifted to the endo-therapy accessory lift position.

During the lifting of the forceps elevator 58, as shown in FIGS. 3B, 4A and 5A, the guide wire 80 is guided along the guide surface 65 of the forceps elevator 58 into the wire-locking groove 66 of the bottom of the guide surface 65. As shown in FIG. 4B, the guide wire 80 is detachably fitted into the wire-locking groove 66.

At this time, as indicated by an arrow P in FIG. 4A, the guide wire 80 is pressed by the forceps elevator 58 to the guide path upper surface wall 49*a* side of the guide path 51 of the tip hard portion 49. A reactive force of a predetermined level or higher indicated by an arrow Fr in FIG. 4A is applied on the guide wire 80 so that the guide wire 80 itself can maintain a straight state. This reactive force Fr is obtained because flexibility of the large diameter portion 81*b* of the core material 81 of the guide wire 80 is low, and a force to maintain the straight state is strong. Accordingly, the reactive force Fr and a pressing force (friction force) when the guide wire 80 is pressed to the guide path upper surface wall 49*a* strongly lock the guide wire 80 in the wire-locking groove 66 to mechanically fix the guide wire 80.

Thus, as shown in FIG. 3B, the guide wire 80 is locked and fixed at the hand side more than the marking 85 by the forceps elevator 58 (locking mechanism).

The operator checks on the locking and fixing of the guide wire 80 by the forceps elevator 58, and then completely pulls out the catheter 90 from the operation section 12 side of the endoscope 10 to the outside of the endo-therapy accessory channel 52.

Subsequently, another endo-therapy accessory to be used next is inserted from the rear end side thereof in a state where the tip of the guide wire 80 is retained near the affected area. At this time, a state is realized where the guide wire 80 is arranged in the inner hole of the endo-therapy accessory. In this manner, the guide wire 80 is arranged, the other endo-therapy accessory is inserted through the endo-therapy accessory channel 52 in the guided state of the guide wire 80, and this endo-therapy accessory is guided to a target portion.

On the other hand, the elevator operation knob 25 is operated before the marking 85 of the guide wire 80 enters the observation visual field 70a of the objective lens 70. This operation is accompanied by pulling of the lift wire 61 shown in FIG. 3A, and the forceps elevator 58 is rotated around the elevator rotation supporting point 59 to be lifted as indicated by a virtual line shown in each of FIGS. 3A and 3B. By this operation, the forceps elevator 58 is lifted to the endo-therapy accessory lift position. During the lifting of the forceps elevator 58, the guide wire 80 is detachably fitted into the wire-locking groove 66.

At this time, as indicated by the arrow P in FIG. 4A, the guide wire 80 is pressed by the forceps elevator 58 to the guide path upper surface wall 49a side of the guide path 51 of the tip hard portion 49. The reactive force of a predetermined level or higher indicated by the arrow Fr in FIG. 4A is applied on the guide-wire 80 so that the guide wire 80 itself can maintain a straight state. For this reactive force Fr, a sufficient force is not obtained because flexibility of the small diameter portion 81a of the core material 81 of the guide wire 80 is low, and a force to maintain the straight state is weak. Accordingly, the reactive force Fr and the pressing force (friction force) when the guide wire 80 is pressed to the guide path upper surface wall 49a weakly lock the guide wire 80 in the wire-locking groove 66. Therefore, when the operator pulls the catheter 90 into the hand side, the guide wire 80 may be pulled in integrally depending on a pulling-in speed. That is, a locking force of the guide wire 80 is weak, and it is difficult to pull the guide wire 80 to the hand side in its retained state.

As described above, according to the embodiment, the following effects are obtained.

By observing the marking 85 disposed in a predetermined position of the guide wire 80 on the observation monitor 70b of the endoscope 10, it is possible to easily determine whether the position can be locked and fixed or not on the forceps elevator 58. Thus, when the guide wire 80 is locked and fixed while the marking 85 of the guide wire 80 is observed, it is possible to pull out/insert the other endo-therapy accessory such as the catheter 90 irrespective of the movement (sliding) of the guide wire 80. When the guide wire 80 is locked and fixed in this manner, it is possible to omit complex operations such as pulling-out of the catheter 90 and relative insertion of the guide wire 80 into the catheter 90 (not moved actually) which the two operators need to repeat in concert many times during the operation.

By disposing the marking 85, it is possible to easily determine whether a position of the guide wire 80 can be locked and fixed or not by the distal end of the insertion portion 11 of the endoscope 10. Accordingly, even if it cannot be actually locked or fixed surely, it is determined that the guide wire 80 can be locked and fixed, whereby an erroneous operation of moving the guide wire 80 which should not be moved from the desired potion can be reduced. Thus, it is possible to increase hand operation efficiency.

According to the embodiment, as shown in FIG. 1A, the marking 85 is disposed in a part of the guide wire 80. However, for example, two colors of a location which enables locking and fixing by the forceps elevator 58 and a location where locking and fixing are impossible may be given to the guide wire 80. Then, a boundary between the two colors works as the marking 85. Additionally, even if the boundary (marking 85) cannot be visually recognized on the observation monitor 70b, by seeing the color of the guide wire 80, it is possible to easily determine whether the location of the guide wire 80 can be locked or not on the forceps elevator 58.

Furthermore, according to the embodiment, the marking 100 is also disposed in the insertion section 91 of the catheter 90 (see FIG. 7A). Thus, in a state where the catheter 90 is arranged on the guide surface 65, and the forceps elevator 58 is lifted to lock and fix the catheter 90 as shown in FIG. 4A, it is possible to pull out the guide wire 80.

Next, a second embodiment will be described with reference to FIG. 9 to FIGS. 13A and 13B. This embodiment is a modified example of the first embodiment. Thus, members similar to those of the foregoing first embodiment are denoted by similar reference numerals, and detailed description thereof will be omitted.

Figure 9:
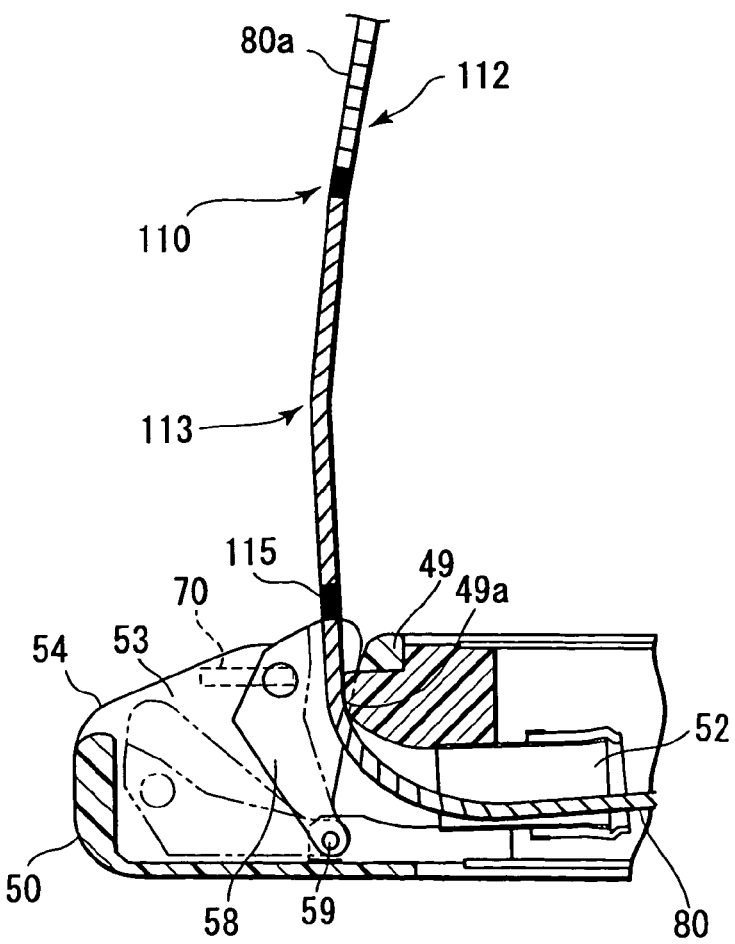
FIG. 9 is a schematic vertical sectional view of a distal end of an endoscope in an endoscopic device according to a second embodiment.

As shown in FIG. 9, a visual field of an objective lens 70 disposed in a distal end 17 of an insertion portion 11 of and endoscope 10 of the embodiment is different from that described above with reference to the first embodiment. According to the embodiment, a guide wire 80 is lifted in a direction of an observation visual field 70a of the objective lens 70 nearly orthogonal to an axial direction of the distal end 17 of the insertion portion 11 of the endoscope 10. At this time, a tip of the guide wire 80 is disposed on the observation monitor 70b shown in FIG. 5B for the first time when the tip of the guide wire 80 is set in a position apart by 5 mm to 30 mm above the objective lens 70.

As shown in FIG. 10A, in the guide wire 80 of the embodiment, first to fourth markings (markers) 110, 111, 112, 113 are disposed. The first marking (the first main-index) 110 is similar to the marking 85 described above with reference to the first embodiment. For this guide wire 80, when a position F of 5 mm to 30 mm from a rear side of the first marking 110 is locked and fixed by a forceps elevator 58 of the distal end 17 of the insertion portion 11 of the endoscope 10, a distance from the fixed position F of the guide wire 80 to the tip is about 50 mm to 250 mm. Further, the forceps elevator 58 never enters the observation visual field 70a of the objective lens 70, that is, it is never displayed on the observation monitor 70b.

Figure 11A:
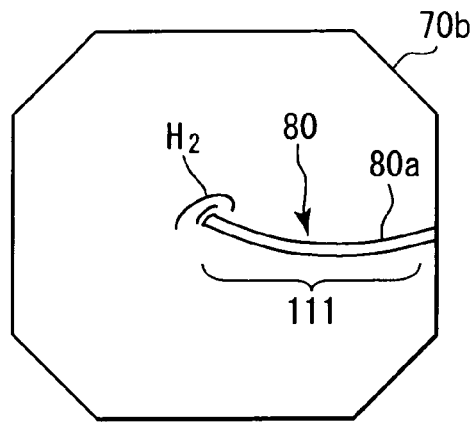
FIG. 11A is a schematic view showing a state where a second marking portion is displayed on a monitor in the endoscopic observation monitor of the endoscopic device of the second embodiment.

The second marking 111 is disposed in a tip of an insertion section 80a of the guide wire 80, i.e., on a cover 82 to cover a small diameter portion 81a of a core material 81. As shown in FIG. 11A, even if the second marking 111 is displayed on the observation monitor 70b of the endoscope 10, the guide wire 80 cannot be locked by the distal end 17 of the insertion portion 11 of the endoscope 10. Preferably, for the second marking 111, the cover 82 itself functions as an index.

Figure 11B:
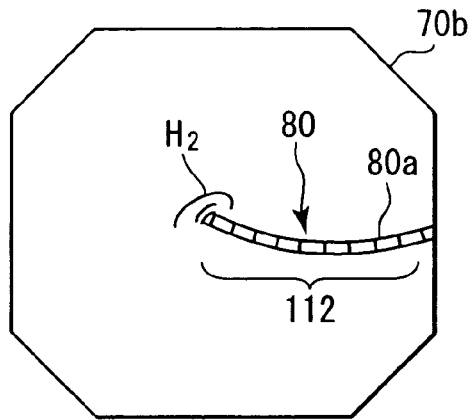
FIG. 11B is a schematic view showing a state where a third marking portion is displayed on the monitor in the endoscopic observation monitor of the endoscopic device of the second embodiment.

As shown in FIG. 10A, the third marking (the first sub-index) 112 is disposed on the cover 82 to cover a tip of a tapered portion 81c of the core material 81 on the front side of the first marking 110. Preferably, for this third marking 112, a portion (a streak portion 112a) recognized to be a ring shape (a streak shaped) in a direction orthogonal to an axial direction of the guide wire 80 is disposed in the outer periphery of the cover 82 of the guide wire 80. As shown in FIG. 11B, even if the third marking 112 is displayed on the observation monitor 70b of the endoscope 10, the guide wire 80 cannot be completely (securely) locked and fixed by the distal end 17 of the insertion portion 11 of the endoscope 10. At this time, when the operator pulls a catheter 90, there is a possibility of associative pulling-out of the guide wire 80 since a locking force of the guide wire 80 is weak. However, even when the third marking 112 is displayed on the observation monitor 70b of the endoscope 10 while the first marking 110 is not displayed on the observation monitor 70b, it is possible to instantaneously determine whether the guide wire 80 can be locked and fixed or not by the distal end 17 of the insertion portion 11 of the endoscope 10. Then, the first marking 110 can be easily guided to a position where it is moved back and forth to be displayed on the observation monitor 70b of the endoscope 10.

Figure 11C:
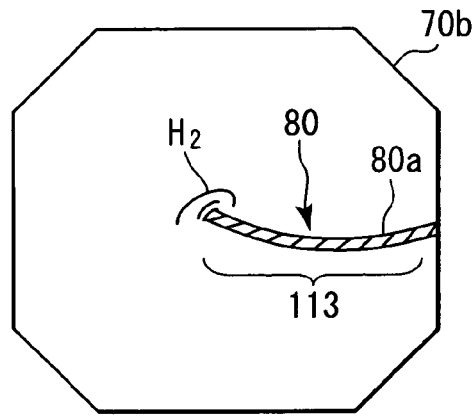
FIG. 11C is a schematic view showing a state where a fourth marking portion is displayed on the monitor in the endoscopic observation monitor of the endoscopic device of the second embodiment.

As shown in FIG. 10A, the fourth marking (the second sub-index) 113 is disposed on the cover 82 to cover a tip of a large diameter portion 81b of the core material 81 in a side after the first marking 110. Preferably, for this fourth marking 113, a portion (a spiral portion 113a) is formed to be recognized as a spiral shape in the outer periphery of the cover 82 of the guide wire 80. As shown in FIG. 11C, if the fourth marking 113 is displayed on the observation monitor 70b of the endoscope 10, the guide wire 80 can be completely locked and fixed by the distal end 17 of the insertion portion 11 of the endoscope 10. That is, even if the fourth marking 113 is displayed on the observation monitor 70b of the endoscope 10 while the first marking 110 is not displayed on the observation monitor 70b, it is possible to instantaneously determine whether the guide wire 80 can be locked and fixed or not by the distal end 17 of the insertion portion 11 of the endoscope 10.

Thus, by disposing the third and fourth markings 112, 113 before and after the first marking 110, even if the first marking 110 cannot be observed, it is possible to easily determine whether the guide wire 80 can be locked (locked and fixed) or not by the forceps elevator 58.

Figure 11D:
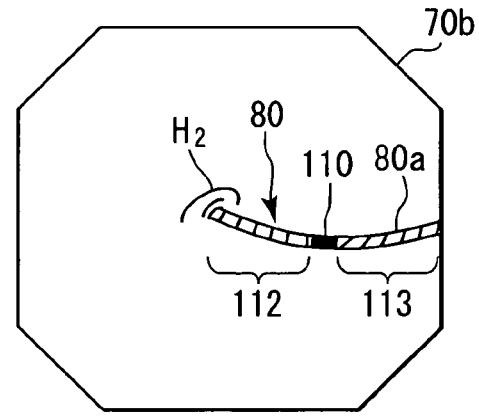
FIG. 11D is a schematic view showing a state where the first, third and fourth marking portions are displayed on the monitor in the endoscopic observation monitor of the endoscopic device of the second embodiment.
Figure 12:
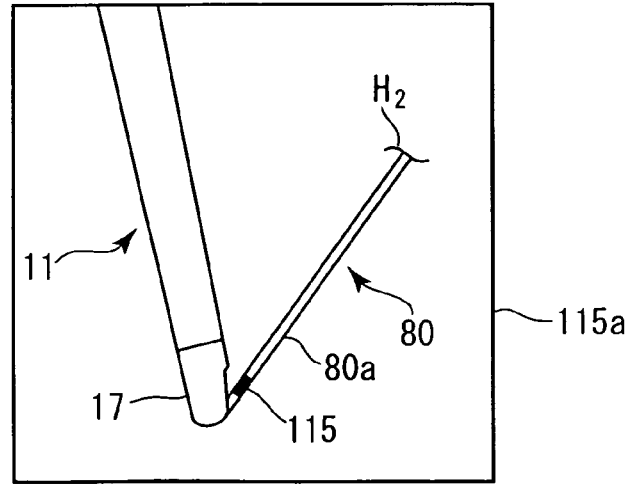
FIG. 12 is a schematic view showing an X-ray fluoroscope monitor in the endoscopic device of the second embodiment.

Incidentally, as shown in FIG. 11D, when the first, third and fourth markings 110, 112, 113 are displayed on the observation monitor 70b of the endoscope 10, as described above with reference to the first embodiment, it is possible to completely lock and fix the guide wire 80 by the distal end 17 of the insertion portion 11 of the endoscope 10.

As shown in FIG. 10B, a ring-shaped or coil-shaped radiopaque X-ray marker (a radiopaque marker) 115 is arranged below the fourth marking 113 in the outer periphery near the rear end of the tapered portion 81c. This guide wire 80 is locked and fixed by the forceps elevator 58 of the distal end 17 of the insertion portion 11 of the endoscope 10 at a fixed position F of 5 mm to 30 mm from the rear side of the first marking 110. At this time, a distance from the fixed position F of the guide wire 80 to the X-ray marker 115 is about 0 mm to 10 mm.

For the X-ray marker 115, a metallic material such as platinum (Pt) or gold (Au) is used. If the patient is irradiated with X-rays when the cover 82 of the outer peripheral position of the X-ray marker 115 of the guide wire 80 is arranged in the body, the X-ray marker 115 is displayed in an X-ray observation image 115a shown in FIG. 12. When this X-ray marker 115 is in the endo-therapy accessory channel 52 of the endoscope 10, it is not displayed in the X-ray observation image 115a. When the X-ray marker 115 is displayed in the X-ray observation image 115a, any part of the guide wire 80 can be locked by the distal end 17 of the insertion portion 11 of the endoscope 10. That is, depending on displaying or non-displaying of the X-ray observation image 115a, the X-ray marker 115 enables the operator for use in determining whether the guide wire 80 is in a position to be locked and fixed or not.

FIGS. 13A and 13B show modified examples of the third and fourth markings 112, 113. As shown in FIG. 13A, in the third and fourth markings 112, 113, streak portions 112b, 113b are disposed side by side at a predetermined interval where streaks are recognized to be thinner closer to the first marking 110, and thicker ring shapes more apart there from. Accordingly, even if the first marking 110 is not displayed on the observation monitor 70b, by reading sizes of the streaks of the streak portions 112b, 113b of the third and fourth markings 112, 113, it is possible to recognize a distance to the first marking 110 or a position.

As shown in FIG. 13B, in the third and fourth markings 112, 113, codes 112c, 113c are disposed side by side where numerical values constituted of natural numbers are smaller closer to the first marking 110, and larger more apart there from. Between these codes 112c and 113c, for example, the streak portions 112b, 113b recognized to be streak shapes are arranged. Between the streak portions 112b and 113b, for example, 5 mm or 10 mm is preferred. Thus, the codes 112c, 113c between the portions recognized as the streak shapes shown in FIG. 13B are substitutes for scales, whereby a distance to the first marking 110 can be easily recognized.

Next, a third embodiment will be described with reference to FIGS. 14A and 14B to FIGS. 17A and 17B. This embodiment is a modified example of the second embodiment, similar members are denoted by similar reference numerals, and detailed description thereof will be omitted.

As shown in FIGS. 14A and 14B, a guide wire 80 as an endo-therapy accessory of the embodiment has a structure similar to that of the guide wire 80 (see FIGS. 10A and 10B) described above with reference to the second embodiment.

As shown in FIG. 14A, fifth to seventh markings 118, 119, 120 are disposed at a hand side of the guide wire 80.

The fifth marking (the second main-index) 118 is formed in a shape similar to that of the first marking 110. That is, a pattern similar to that of the first marking 110 is given to the fifth marking 118. A distance between the first marking 110 and the fifth marking 118 coincides with a distance which combines a total length of an endo-therapy accessory channel 52 of an insertion portion 11 of an endoscope 10 with a minimum distance (5 mm to 30 mm) from an objective lens 70 of a distal end 17 of the insertion portion 11 where the guide wire 80 is displayed in its observation visual field 70a.

The sixth marking (the third sub-index) 119 is formed in a shape similar to that of the third marking 112. That is, a pattern similar to that of the third marking 112 is given to the sixth marking 119. A distance between the third marking 112 and the sixth marking 119 coincides with the distance between the first marking 110 and the fifth marking 118.

The seventh marking (the fourth sub-index) 120 is formed in a shape similar to that of the fourth marking 113. That is, a pattern similar to that of the fourth marking 113 is given to the seventh marking 120. A distance between the fourth marking 113 and the seventh marking 120 coincides with the distance between the first marking 110 and the fifth marking 118.

Thus, the fifth to seventh markings 118, 119, 120 of the guide wire 80 are moved associatively with the first, third and fourth markings 110, 120, 113.

As shown in FIG. 15B, when the second marking 111 is observed on the observation monitor 70b, the sixth marking 119 is projected more from a biopsy valve 26 disposed near a boundary between the insertion portion 11 and the operation section 12 of the endoscope 10 to a rear side as shown in FIG. 15A. That is, when the sixth marking 119 is projected more from the biopsy valve 26 to the rear side, merely by seeing a hand side of the biopsy valve 26, it is possible to recognize that the guide wire 80 cannot be locked by the distal end 17 of the insertion portion 11 of the endoscope 10.

As shown in FIG. 15D, when the third marking 112 is observed on the observation monitor 70b, the sixth marking 119 coincides with a rear end of the forceps 26 as shown in FIG. 15C. That is, when the sixth marking 119 coincides with the rear end of the biopsy valve 26, merely by seeing the hand side of the biopsy valve 26, it is possible to recognize that even if the guide wire 80 is locked by the distal end 17 of the insertion portion 11 of the endoscope 10, there is a possibility of associative pulling-out of the guide wire 80 when the operator pulls the catheter 90.

As shown in FIG. 16B, when the fourth marking 113 is observed on the observation monitor 70b, the seventh marking 120 coincides with the rear end of the biopsy valve 26 as shown in FIG. 16A. That is, when the seventh marking 120 coincides with the rear end of the biopsy valve 26, merely by seeing the hand side of the biopsy valve 26, it is possible to recognize that the guide wire 80 can be completely locked and fixed by the distal end 17 of the insertion portion 11 of the endoscope 10.

As shown in FIG. 16D, when the first, third and fourth markings 110, 112, 113 are observed on the observation monitor 70b, the fifth marking 118 coincides with the rear end of the forceps 26 as shown in FIG. 16C. At this time, as in a case where the seventh marking 120 coincides with the rear end of the biopsy valve 26, merely by seeing the hand side of the biopsy valve 26, it is possible to recognize that the guide wire 80 can be completely locked and fixed by the distal end 17 of the insertion portion 11 of the endoscope 10.

Thus, the operator can check on the locking and fixing enable position of the guide wire 80 by both of the observation monitor 70b of the endoscope 10 and the fifth to seventh markings 118, 119, 120 of the hand side.

Figure 17A:
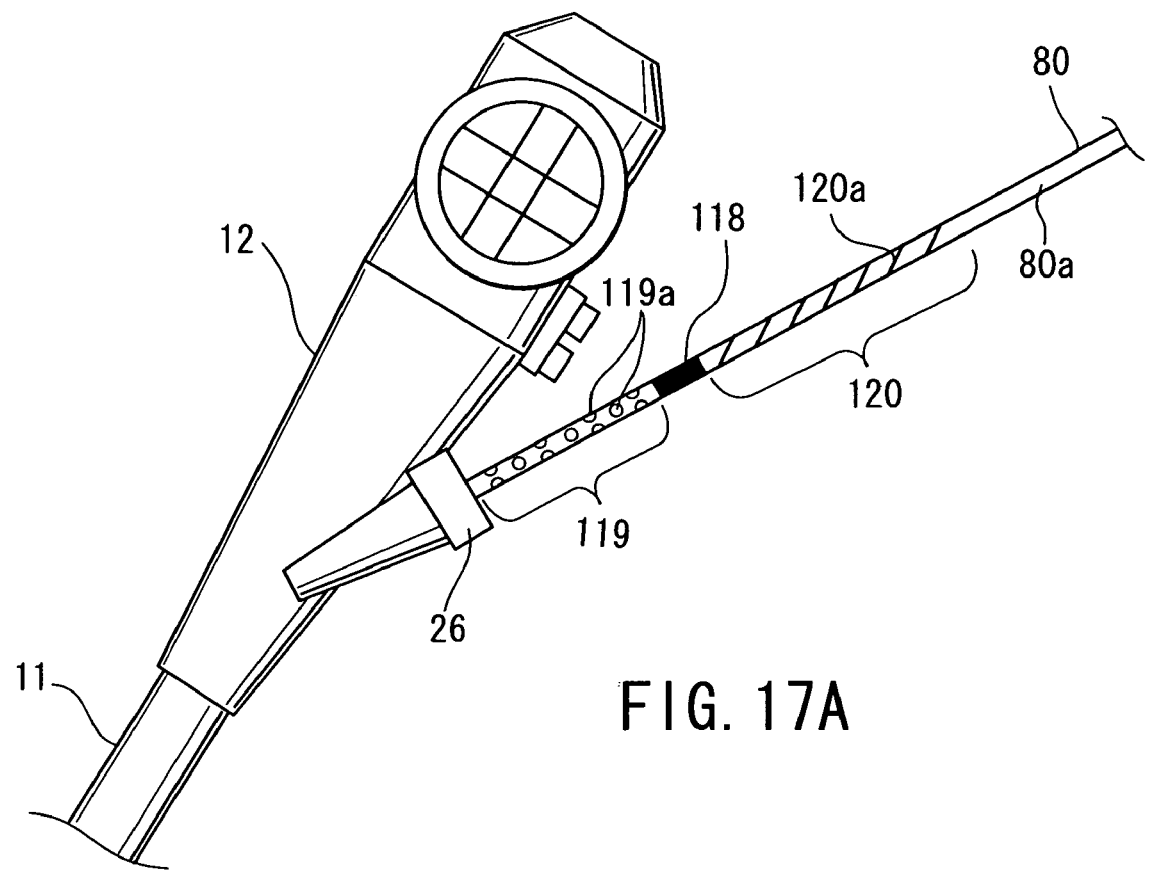
FIG. 17A is a schematic view showing the hand side in the endoscope of the endoscopic device of the third embodiment where the deformed sixth marking portion coincides with the base end of the biopsy valve.
Figure 17B:
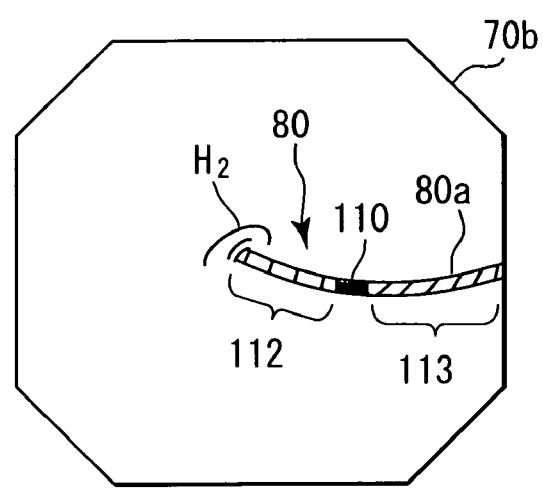
FIG. 17B is a schematic view showing the endoscopic observation monitor displayed when the guide wire is in a state shown in FIG. 17A.

FIG. 17A shows a modified example of the sixth and seventh markings 119, 120. As shown in FIG. 17A, a number of dimples 119a are formed in the sixth marking 119. Touch (hand feeling) when the operator grips the dimples 119a is clearly different from that when he grips the cover 82 of the guide wire 80.

On the other hand, a spiral (a screw-shaped) portion 120a is formed in the seventh marking 120. Touch when the operator grips this spiral portion 120a is clearly different from that when he grips the cover 82 of the guide wire 80 and the dimples 119a of the sixth marking 119.

Therefore, the operator can recognize the positions of the fifth to seventh markings 118, 119, 120 with respect to the rear end of the biopsy valve 26 of the endoscope 10 by touch without observing the hand side when the guide wire 80 is inserted into/pulled out from the biopsy valve 26. Thus, even when observing other portion without observing the observation monitor 70b shown in FIG. 17B, the operator can easily recognize the position where the guide wire 80 can be locked by the distal end 17 of the insertion portion 11 of the endoscope 10.

The embodiment discloses the constitution which has both of the tip side markings 110, 112, 113, and the hand side markings 118, 119, 120. Since the tip side markings 110, 112, 113 and the hand side markings 118, 119, 120 have similar roles, for example, the tip side marking 110, 112, 113 may be omitted.

Next, a fourth embodiment will be described with reference to FIGS. 18A and 18B and FIGS. 19A to 19D. This embodiment is a modified example of the first embodiment, similar members are denoted by similar reference numerals, and detailed description thereof will be omitted.

Figures 18A, 18B:
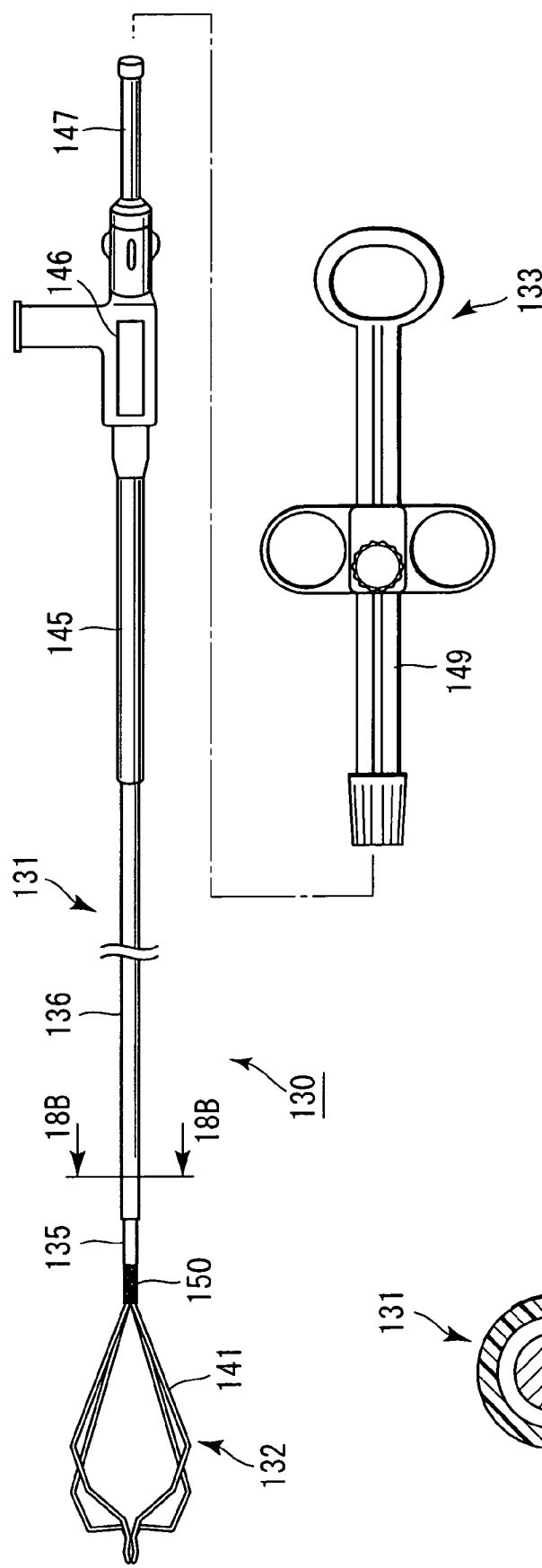
FIG. 18A is a schematic side view showing a basket type forceps of an endoscopic device according to a fourth embodiment.
FIG. 18B is a sectional view cut along the lien 18B—18B of the basket type forceps shown in FIG. 18A.

As shown in FIG. 18A, an endo-therapy accessory inserted through an endo-therapy accessory channel 52 of an insertion portion 11 of an endoscope 10 is a basket type forceps 130. This basket type forceps 130 includes a thin and long flexible insertion section 131, a treatment section 132 disposed in a tip of the insertion section 131, and an operation section 133 disposed in a rear end of the insertion section 131 to open/close the treatment section 132.

The insertion section 131 includes a power transmission wire 135 to transmit power when the operation section 133 is operated, and a cover sheath 136 to cover an outer periphery of the power transmission wire 135 (see FIG. 18B). This cover sheath 136 is made of a material such as polyethylene or PTFE so as to be easily inserted into a winding bile duct or the like. The power transmission wire 135 is made of a super-elastic alloy material such as a nickel titanium alloy, and has flexibility.

A rear end of the treatment section 132 is connected to a tip of the power transmission wire 135. Each of the rear end and the tip of the treatment section 132 are retained at one point, and an elongation portion (basket) 141 is formed to be freely contracted/expanded (opened/closed) between the rear end and the tip. This elongation portion 141 is formed in a basket shape by, e.g., four small diameter wires.

The operation section 133 is detachably arranged in the rear end of the power transmission wire 135. A sheath holding section 145 is disposed in the rear end of the cover sheath 136. A cock 146 is disposed in the rear end of the sheath holding section 145. An operation handle attaching/detaching section 147 is disposed in a rear end of the cock 146. An operation handle 149 can be detachably attached to the operation handle attaching/detaching section 147.

The sheath holding section 145, the cock 146 and the operation handle attaching/detaching section 147 can be integrally removed from the rear end side of the operation handle attaching/detaching section 147. In a state where the sheath holding section 145, the cock 146 and the operation handle attaching/detaching section 147 are removed, a sheath 136 can be pulled out from the rear end of power transmission wire 135. In place of the removed cover sheath 136, a later-described metallic material coil sheath 157 can be fixed.

Additionally, the marking (e.g., X-ray marker) 150 of the basket type forceps 130 is disposed in, for example, the rear end of the basket type treatment section 132, i.e., in the tip of the power transmission wire 135.

Next, an operation of the endo-therapy accessory (basket type forceps 130) of the embodiment will be described by referring to FIGS. 19A to 19D.

Figure 19A:
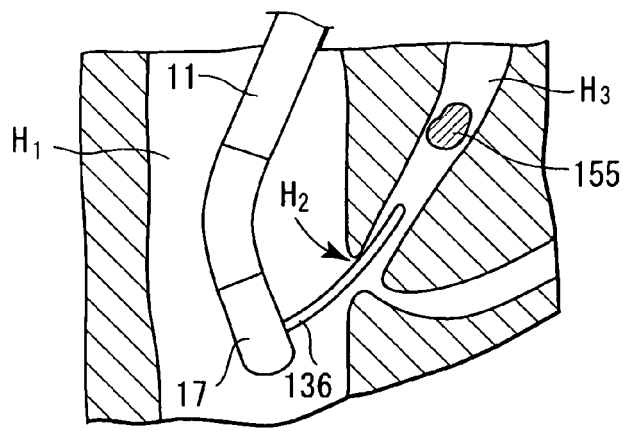
FIG. 19A is a schematic view showing an operation of an endoscopic device according to a fourth embodiment, where a covering sheath is inserted into a bile duct while a basket type endo-therapy accessory is stashed in the covering sheath.

As shown in FIG. 19A, this endo-therapy accessory is used when a calculus 155 in a bile duct H3 is discharged from a papilla H2 into a duodenum H1. Specifically, as shown in FIG. 19A, the basket type treatment section 132 is inserted into the bile duct H3 in its housed state in the cover sheath 136. The tip of the cover sheath 136 is positioned near the calculus 155.

Figure 19B:
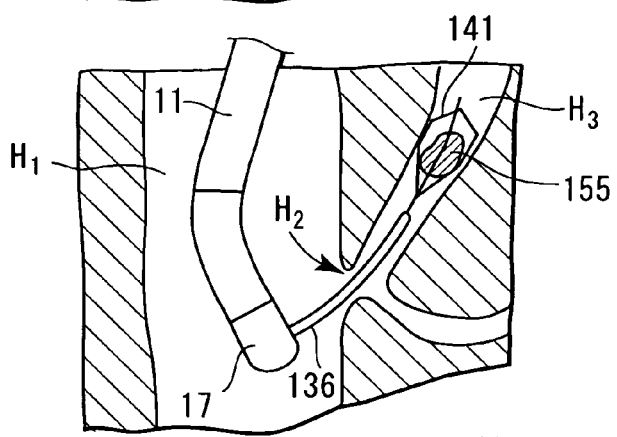
FIG. 19B is a schematic view showing the operation of the endoscopic device of the fourth embodiment, where a calculus is taken into a basket while the basket type endo-therapy accessory is spread out from a tip of the covering sheath.

As shown in FIG. 19B, the basket type treatment section 132 is spread from the tip of the cover sheath 136. The calculus 155 is taken into the basket (elongation portion) 141 by the basket type treatment section 132. In this state, the basket type treatment section 132 is pulled out from the bile duct H3 to remove the calculus 155 from the bile duct H3 into the duodenum H1.

If the calculus 155 or the like is too large to be pulled out from the bile duct H3, an operation is carried out to pull the basket type treatment section 132 into the cover sheath 136 while the calculus 155 is retained in the basket 141. Accordingly, the calculus 155 is compressed, and crushed into pieces to be discharged.

Figure 19C:
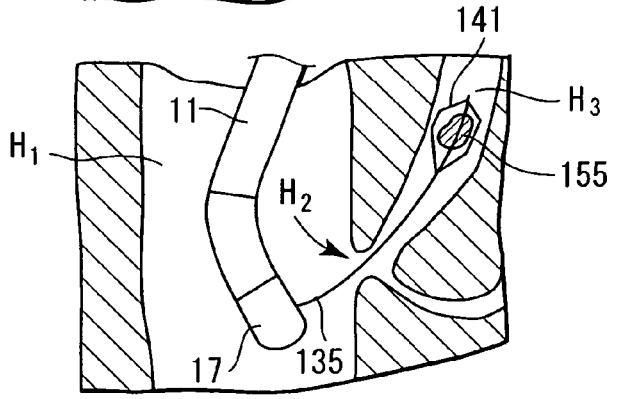
FIG. 19C is a schematic view showing the operation of the endoscopic device of the fourth embodiment, where the covering sheath is pulled out while the calculus is taken into the basket of the basket type endo-therapy accessory.
Figure 19D:
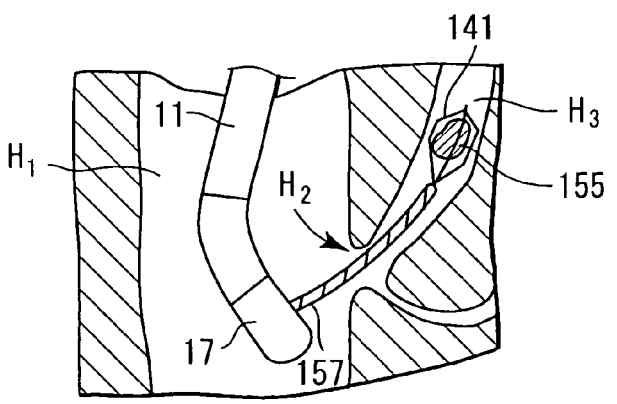
FIG. 19D is a schematic view showing the operation of the endoscopic device of the fourth embodiment, where a coil sheath made of a metallic material is inserted along a power transmission wire.
Figure 20A:
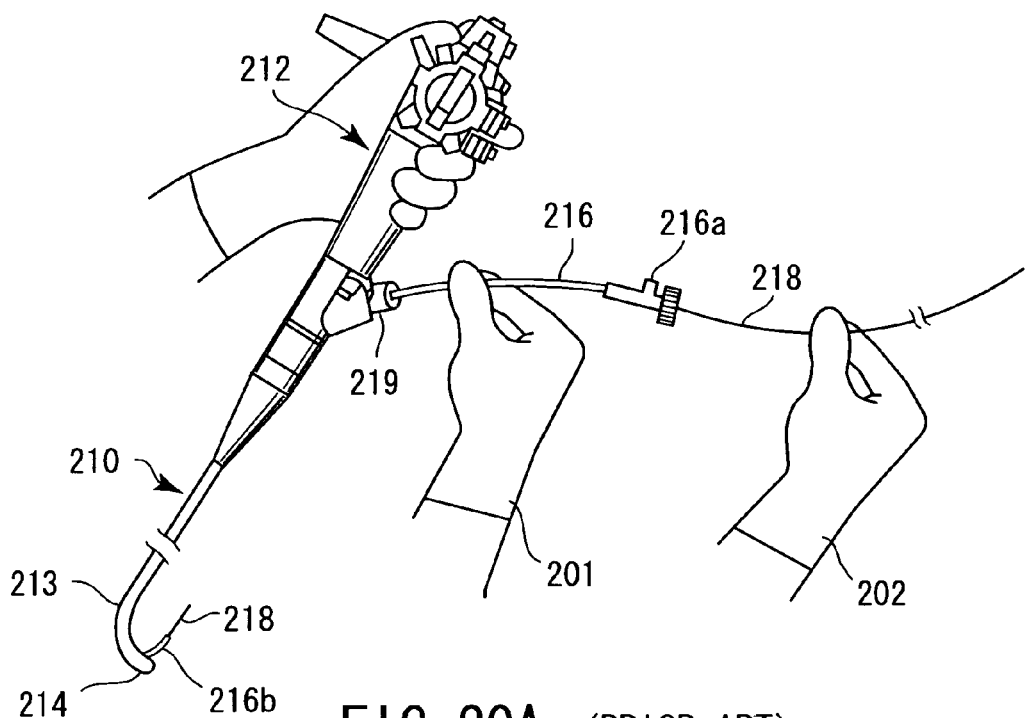
FIG. 20A is a schematic view showing an operation of an endoscopic device according to a conventional art.
Figure 20B:
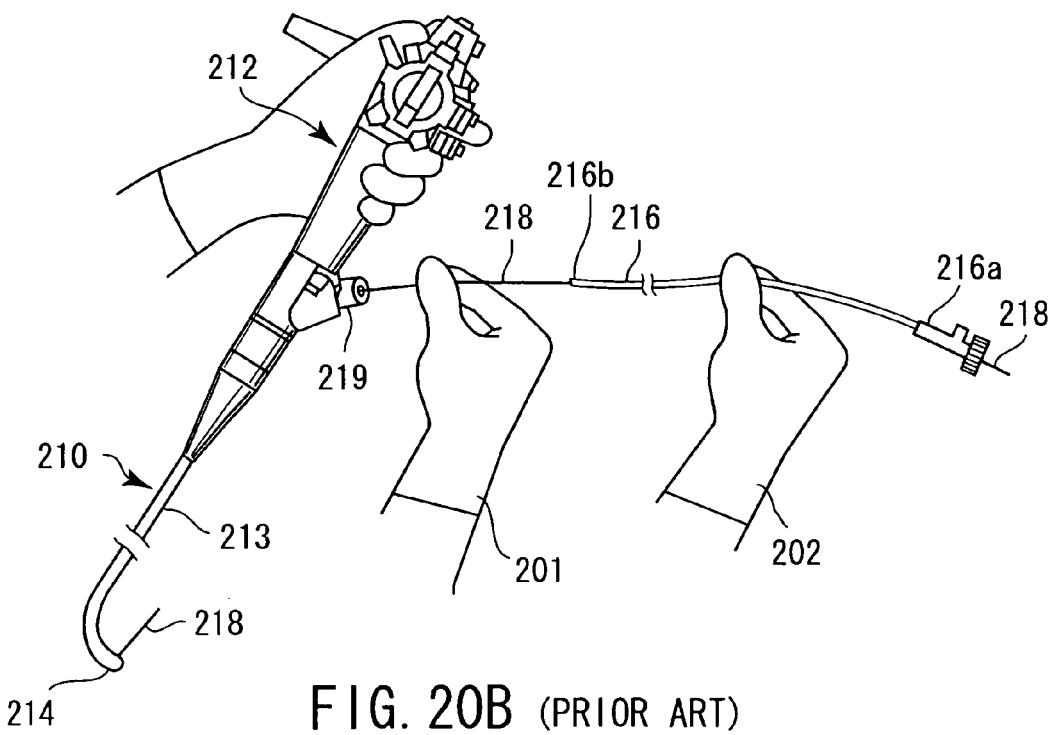
FIG. 20B is a schematic view showing the operation of the endoscopic device of the conventional art.

If the calculus 155 is hard, even if the basket (thin diameter wire) is pulled in, the cover sheath 136 is deformed, which disables crushing of the calculus 155. In such a case, as shown in FIG. 19C, the cover sheath 136 is pulled out while the calculus 155 is retained in the basket type treatment section 132.

When the cover sheath 136 is removed, in a state where the marking 150 on the power transmission wire 135 is checked by an image of the endoscope, the forceps elevator 58 is lifted to lock the power transmission wire 135. At this time, after the operation handle 149 of the operation section 133 is removed, the cover sheath 136 is removed. In a position of the cover sheath 136 before the removal, a coil sheath 157 made of a metallic material and higher in rigidity than the cover sheath 136 is inserted along the outer periphery of the power transmission wire 135 (see FIG. 19D). The operation handle 149 of the operation section 133 is fixed to a rear side of the coil sheath 157.

Then, a tip of the coil sheath 157 is inserted into the bile duct H3 while the locking of the marking 150 on the power transmission wire 135 is released. In this state, the calculus 155 is pulled into the coil sheath 157 to be crushed.

As described above, according to the embodiment, the following effect is obtained.

For example, when crushing of the calculus 155 is difficult, since the cover sheath 136 can be quickly exchanged by the coil sheath 157, it is possible to shorten time necessary for a series of curative operations.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endo-therapy accessory-fixing method which fixes an endo-therapy accessory by a distal end of an insertion section of an endoscope, including:
   inserting the endoscope which has a forceps elevator into a patient,
   inserting the endo-therapy accessory into the endoscope, the endo-therapy accessory used in combination with an endoscope which has a forceps elevator, the endo-therapy accessory comprising:
   an insertion portion of the endo-therapy accessory to be inserted into the endoscope;
   wherein the insertion portion of the endo-therapy accessory comprises:
   a forceps elevator fixing section set in a range of passing the elevator, and fixed when the elevator is lifted; and
   a main index for use in determining whether a part of the elevator fixing portion, which is more proximal than a far end of the fixing portion, is located on the elevator;
   recognizing a position of the main index by an observation image of an observation device of the endoscope, and
   operating the elevator to fix the endo-therapy accessory in the endoscope.

2. An endo-therapy accessory system comprising:
   an endoscope including an insertion section, the insertion section comprising:
   a distal end portion;
   a proximal end portion;
   an observation device disposed on the distal end portion;
   a channel inserted from the distal end portion to the proximal end portion, wherein the channel includes distal and proximal side openings, therapeutic devices inserted from the proximal side opening being configured to project from the distal side opening; and
   a forceps elevator disposed on the distal end portion and disposed on the distal side of the channel, the forceps elevator lifts the inserted therapeutic devices;
   an endo-therapy accessory including tip and base ends, the endo-therapy accessory configured to be inserted in the channel;
   a forceps elevator fixing section disposed on the endo-therapy accessory, the forceps elevator fixing section controlling relative movement of the endo-therapy accessory with respect to the insertion section of the endoscope by engaging with the forceps elevator according to the lifting thereof so as to arrange the fixing section on the forceps elevator when the endo-therapy accessory is inserted in the channel; and
   a main index disposed in the endo-therapy accessory so as to be arranged within a field of view of the observation device when the fixing section is located on the elevator.

3. The endo-therapy accessory system according to claim 2, wherein the main index includes an X-ray marker recognized by an X-ray observation image.

4. The endo-therapy accessory system according to claim 2, further including a distal end subindex disposed on a tip side of the endo-therapy accessory and more distal than the main index, the distal end subindex being disposed on the tip side of the endo-therapy accessory so as to be arranged within the field of view of the observation device when the fixing section is deviated from the forceps elevator.

5. The endo-therapy accessory system according to claim 2, further including a proximal side subindex disposed on a tip of the endo-therapy accessory and more proximal than the main index, the proximal side subindex being disposed on the tip side of the endo-therapy accessory so as to be arranged within the field of view of the observation device when the fixing section is located on the forceps elevator.

6. The endo-therapy accessory system according to claim 2, wherein the endo-therapy accessory is a guide wire.

7. The endo-therapy accessory system according to claim 2, further including a proximal side main index disposed on a tip side of the endo-therapy accessory and more proximal than the main index, the proximal side main index being disposed on the tip side of the endo-therapy accessory so as to be arranged at the proximal side opening of the channel when the fixing section is located on the forceps elevator.

8. The endo-therapy accessory system according to claim 2, the endo-therapy accessory further comprising:
   a core member extending along an axis of the endo-therapy accessory, including a distal end portion and a proximal end portion thicker than the distal end portion; and
   a cover for covering the outer peripheral surface of the core member,
   wherein the fixing section is disposed in the endo-therapy accessory so as to be arranged on the proximal portion of the core member.

9. The endo-therapy accessory system according to claim 8, wherein the core member is formed continuously so as to taper from the distal end portion to the proximal end portion.

10. The endo-therapy accessory system according to claim 1, wherein the endo-therapy accessory includes a distal end portion and a proximal end portion, the proximal end portion has rigidity to bending larger than that of the distal end portion, and
    the fixing section is disposed on the proximal end portion of the endo-therapy accessory.

11. The endo-therapy accessory system according to claim 10, further including a proximal side subindex disposed on a tip side of the endo-therapy accessory and more proximal than the main index, the proximal side subindex being disposed so as to be arranged within the field view of the observation device when the fixing section is located on the forceps elevator.

12. The endo-therapy accessory system according to claim 10, the endo-therapy accessory further comprising:

a core member extending along an axis of the endo-therapy accessory, including a thin portion located on the distal end portion of the endo-therapy accessory and a thick portion located on the proximal end portion of the endo-therapy accessory; and a cover for covering the outer peripheral surface of the core member.

* * * * *